(12) United States Patent
Kashyap

(10) Patent No.: US 11,884,958 B2
(45) Date of Patent: Jan. 30, 2024

(54) ASSESSING AND TREATING FUNCTIONAL GASTROINTESTINAL DISORDERS

(71) Applicant: Mayo Foundation for Medical Education and Research, Rochester, MN (US)

(72) Inventor: Purna C. Kashyap, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 443 days.

(21) Appl. No.: 16/857,965

(22) Filed: Apr. 24, 2020

(65) Prior Publication Data

US 2020/0399673 A1    Dec. 24, 2020

Related U.S. Application Data

(60) Provisional application No. 62/840,867, filed on Apr. 30, 2019.

(51) Int. Cl.
  *C12Q 1/06* (2006.01)
  *C09D 175/08* (2006.01)

(52) U.S. Cl.
  CPC .............. *C12Q 1/06* (2013.01); *C09D 175/08* (2013.01)

(58) Field of Classification Search
  None
  See application file for complete search history.

(56) References Cited

U.S. PATENT DOCUMENTS

| | | | |
|---|---|---|---|
| 10,184,940 B2 | 1/2019 | Singh et al. | |
| 2015/0259728 A1 | 9/2015 | Cutliffe et al. | |
| 2015/0307924 A1 | 10/2015 | Tuk et al. | |
| 2016/0139148 A1 * | 5/2016 | Westin | C07K 16/44 435/7.92 |
| 2016/0271188 A1 | 9/2016 | Berry et al. | |

FOREIGN PATENT DOCUMENTS

| | | | | |
|---|---|---|---|---|
| WO | WO 2017118924 | | 7/2017 | |
| WO | WO-2018071534 A1 * | | 4/2018 | ............. A61K 35/38 |
| WO | WO 2019014714 | | 1/2019 | |
| WO | WO-2019067087 A1 * | | 4/2019 | ............. A23K 10/18 |

OTHER PUBLICATIONS

Casen, C. et al. 2015. Deviations in human gut microbiota: a novel diagnostic test for determining dysbiosis in patients with IBS or IBD. Alitmentary Pharmacology and Therapeutics 42: 71-83; specif. pp. 72, 73, 78, Suppl. Data.*

Zhang, T. et al. 2022. Efficacy of probiotics for irritable bowel syndrome: a systematic review and network meta-analysis. Frontiers in Cellular and Infection Microbiology 12: 1-15; specif. p. 1.*
Al-Ghalith et al., "SHI7 Is a Self-Learning Pipeline for Multipurpose Short-Read DNA Quality Control," mSystems, May/Jun. 2018, 3(3):e00202-17, 8 pages.
Anders et al., "HTSeq—a Python framework to work with high-throughput sequencing data," Bioinformatics, Jan. 2015, 31(2):166-169.
Banhegyi et al., "Ascorbate Metabolism and its Regulation in Animals," Free Radic. Biol. Medicine, 1997, 23(5):793-803.
Bardhan et al., "Diagnosis of Bacterial Overgrowth after Culturing Proximal Small-Bowel Aspirate Obtained during Routine Upper Gastrointestinal Endoscopy," Scand. J. Gastroenterology, 1992, 27(3):253-256.
Bauer et al., "Diagnosis of small intestinal bacterial overgrowth in patients with cirrhosis of the liver: poor performance of the glucose breath hydrogen test," J. Hepatology, Sep. 2000, 33(3):382-386.
Bhattarai et al., "Irritable bowel syndrome: a gut microbiota-related disorder?," Am. J. Physiol. Gastrointest. Liver Physiology, Jan. 2017, 312(1):G52-G62.
Booijink et al., "High temporal and inter-individual variation detected in the human ileal microbiota," Environ. Microbiology, Dec. 2010, 12(12):3213-3227.
Bures et al., "Small intestinal bacterial overgrowth syndrome," World J. Gastroenterology, Jun. 28, 2010, 16(24):2978-2990.
Caporaso et al., "QIIME allows analysis of high-throughput community sequencing data," Nat. Methods, May 2010, 7(5)335-336.
Carding et al., "Dysbiosis of the gut microbiota in disease," Microb. Ecol. Health Disease, Feb. 2015, 26:26191, 9 pages.
Chen et al., "GMPR: A robust normalization method for zero-inflated count data with application to microbiome sequencing data," PeerJ, Apr. 2, 2018, 6:e4600, 20 pages.
Chung et al., "Differences of microbiota in small bowel and faeces between irritable bowel syndrome patients and healthy subjects," Scand. J. Gastroenterology, Nov. 2015, 51(4):410-419.
ClinicalTrials.gov [online], "Small Bowel Microbiota Characterization in Healthy Individuals Before and After Consumption of a Western Diet (Microbiota)," NCT03266536, last updated Feb. 11, 2020, retrieved on Jan. 26, 2021, retrieved from URL<https://clinicaltrials.gov/ct2/show/NCT03266536>, 13 pages.
Corazza et al., "The Diagnosis of Small Bowel Bacterial Overgrowth: Reliability of Jejunal Culture and Inadequacy of Breath Hydrogen Testing," Gastroenterology, Feb. 1990, 98(2):302-309.
Dlugosz et al., "No difference in small bowel microbiota between patients with irritable bowel syndrome and healthy controls," Sci. Reports, Feb. 17, 2015, 5:8508, 10 pages.
Drossman, "Functional Gastrointestinal Disorders: History, Pathophysiology, Clinical Features, and Rome IV," Gastroenterology, May 2016, 150(6):1262-1279.

(Continued)

*Primary Examiner* — Michael Barker
*Assistant Examiner* — Sharon M. Papciak
(74) *Attorney, Agent, or Firm* — Fish & Richardson P.C.

(57) ABSTRACT

This document provides methods and materials involved in assessing and/or treating a mammal having a functional gastrointestinal disorder (FGID) such as irritable bowel syndrome (IBS). For example, methods and materials provided herein can be used for determining if a mammal having a FGID is likely to respond to a particular FGID treatment. This document also provides methods and materials for treating a mammal having a FGID.

6 Claims, 14 Drawing Sheets

Specification includes a Sequence Listing.

(56) References Cited

OTHER PUBLICATIONS

El Aidy et al., "The small intestine microbiota, nutritional modulation and relevance for health," Curr. Opin. Biotechnology, Apr. 2015, 32:14-20.
ENA Accession No. PRJEB31438, "Small intestinal microbial dysbiosis," Mar. 1, 2019, retrieved on Jan. 26, 2021, retrieved from URL<https://www.ebi.ac.uk/ena/browser/view/PRJEB31438>, 2 pages.
ENA Accession No. PRJEB31439, "Dietary impact on small intestinal microbiome," Mar. 1, 2019, retrieved on Jan. 26, 2021, retrieved from URL<https://www.ebi.ac.uk/ena/browser/view/PRJEB31439>, 2 pages.
Ford et al., "Small Intestinal Bacterial Overgrowth in Irritable Bowel Syndrome: Systematic Review and Meta-analysis," Clin. Gastroenterol. Hepatology, Dec. 2009, 7(12):1279-1286.
Fukuda et al., "Bifidobacteria can protect from enteropathogenic infection through production of acetate," Nature, Jan. 27, 2011, 469(7331):543-547.
GEO Series GSE128189, "Small intestinal microbial dysbiosis underlies symptoms associated with functional gastrointestinal disorders," Mar. 14, 2019, retrieved on Jan. 26, 2021, retrieved from URL<https://www.ncbi.nlm.nih.gov/geo/query/acc.cgi?acc=GSE128189>, 2 pages.
Ghoshal et al., "A proof-of-concept study showing antibiotics to be more effective in irritable bowel syndrome with than without small-intestinal bacterial overgrowth: a randomized, double-blind, placebo-controlled trial," Eur. J. Gastroenterol. Hepatology, Mar. 2016, 28(3):281-289.
Ghoshal et al., "Small Intestinal Bacterial Overgrowth and Irritable Bowel Syndrome: A Bridge between Functional Organic Dichotomy," Gut and Liver, Mar. 2017, 11(2):196-208.
Github.com [online], "BURST enables optimal exhaustive DNA alignment for big data," Feb. 3, 2017, last updated Apr. 30, 2020, retrieved on Jan. 26, 2021, retrieved from URL<https://github.com/knights-lab/BURST>, 8 pages.
Github.com [online], "Small Bowel Dysbiosis," Feb. 27, 2019, retrieved on Jan. 26, 2021, retrieved from URL<https://github.com/RRShieldsCutler/small_bowel_dysbiosis>, 2 pages.
Gohl et al., "Systematic improvement of amplicon marker gene methods for increased accuracy in microbiome studies," Nat. Biotechnology, Sep. 2016, 34(9):942-949.
Grover et al., "Small intestinal bacterial overgrowth in irritable bowel syndrome: association with colon motility, bowel symptoms, and psychological distress," Neurogastroenterol. Motility, Sep. 2008, 20(9):998-1008.
Hamilton et al., "Assessment and Significance of Bacterial Overgrowth in the Small Bowel," Q. J. Medicine, Apr. 1970, 39(154):265-285.
Hansen et al., "Removing technical variability in RNA-seq data using conditional quantile normalization," Biostatistics, Apr. 2012, 13(2):204-216.
Kalari et al., "MAP-RSeq: Mayo Analysis Pipeline for RNA sequencing," BMC Bioinformatics, Jun. 2014, 15:224, 11 pages.
Karatzoglou et al., "kernlab—An S4 Package for Kernel Methods in R," J. Stat. Software, Nov. 2004, 11(9), 20 pages.
King et al., "Comparison of the 1-Gram [14C]Xylose, 10-Gram Lactulose-H2, and 80-Gram Glucose-H2 Breath Tests in Patients With Small Intestine Bacterial Overgrowth," Gastroenterology, Dec. 1986, 91(6):1447-1451.
King et al., "Small Intestine Bacterial Overgrowth," Gastroenterology, May 1979, 76(5 Pt 1)1035-1055.
Kostic et al., "The Microbiome in Inflammatory Bowel Disease: Current Status and the Future Ahead," Gastroenterology, May 2014, 146(6):1489-1499.
Kursa et al., "Feature Selection with the Boruta Package," J. Stat, Software, Sep. 16, 2010, 36(11), 13 pages.
Langille et al., "Predictive functional profiling of microbial communities using 16S rRNA marker gene sequences," Nat. Biotechnology, Sep. 2013, 31(9):814-821.

Mattiello et al., "A web application for sample size and power calculation in case-control microbiome studies," Bioinformatics, Jul. 1, 2016, 32(13):2038-2040.
Maxwell et al., "Antibiotics Increase Functional Abdominal Symptoms," Am. J. Gastroenterology, Jan. 2002, 97(1):104-108.
MetaboLights Accession No. MTBLS876, "Small intestinal microbial dysbiosis underlies symptoms associated with functional gastrointestinal disorders," Mar. 29, 2019, retrieved on Jan. 26, 2021, retrieved from URL<https://www.ebi.ac.uk/metabolights/MTBLS876/descriptors>, 4 pages.
Moayyedi et al., "The Effect of Fiber Supplementation on Irritable Bowel Syndrome: A Systematic Review and Meta-analysis," Am. J. Gastroenterology, Sep. 2014, 109(9):1367-1374.
Montassier et al., "Cloud: a non-parametric detection test for microbiome outliers," Microbiome, Aug. 2018, 6(1):137, 11 pages.
Needleman et al., "A General Method Applicable to the Search for Similarities in the Amino Acid Sequence of Two Proteins," J. Mol. Biology, Mar. 1970, 48(3):443-453.
Nguyen et al., "Abnormal postprandial duodenal chyme transport in patients with long standing insulin dependent diabetes mellitus," Gut, Nov. 1997, 41(5):624-631.
Peng et al., "Butyrate Enhances the Intestinal Barrier by Facilitating Tight Junction Assembly via Activation of AMP-Activated Protein Kinase in Caco-2 Cell Monolayers," J. Nutrition, Sep. 2009, 139(9):1619-1625.
Peters et al., "Constipation-Predominant Irritable Bowel Syndrome Females Have Normal Colonic Barrier and Secretory Function," Am. J. Gastroenterology, Jun. 2017, 112(6):913-923.
Quigley et al., "Motility of the Terminal Ileum and Ileocecal Sphincter in Healthy Humans," Gastroenterology, Oct. 1984, 87(4):857-866.
Saffouri et al., "A Subset of Symptomatic Patients Exhibit Small Intestinal Dysbiosis Irrespective of Quantitative Duodenal Aspirate Culture Results," AGA Abstracts, May 2018, Sa1218:S-281.
Saffouri et al., "A subset of symptomatic patients exhibit small intestinal dysbiosis irrespective of quantitative duodenal aspirate culture results," Poster, presented at Proceedings of Digestive Disease Week 2018, Washington, DC, USA, Jun. 2, 2018, 1 page.
Saffouri et al., "Small intestinal microbial dysbiosis underlies symptoms associated with functional gastrointestinal disorders," Nat. Communications, May 1, 2019, 10:2012, 11 pages.
Sajjad et al., "Ciprofloxacin suppresses bacterial overgrowth, increases fasting insulin but does not correct low acylated ghrelin concentration in non-alcoholic steatohepatitis," Aliment. Pharmacol. Therapeutics, Aug. 2005, 22(4):291-299.
Segata et al., "Metagenomic biomarker discovery and explanation," Genome Biology, Jun. 24, 2011, 12(6):R60.
Simren et al., "Intestinal microbiota in functional bowel disorders: a Rome foundation report," Gut, Jan. 2013, 62(1):159-176.
Sonnenburg et al., "Starving our Microbial Self: The Deleterious Consequences of a Diet Deficient in Microbiota-Accessible Carbohydrates," Cell Metabolism, Nov. 4, 2014, 20(5):779-786.
Tabaqchali et al., "Influence of Abnormal Bacterial Flora on Small Intestinal Function." Proc. R. Soc. Medicine, Dec. 1966, 59(12):1244-1246.
Trapnell et al., "TopHat: discovering splice junctions with RNA-Seq," Bioinformatics, May 1, 2009, 25(9):1105-1111.
Tsai et al., "Oxidative stress: an important phenomenon with pathogenetic significance in the progression of acute pancreatitis," Gut, Jun. 1998, 42(6):850-855.
Walters et al., "Detection of bacterial overgrowth in IBS using the lactulose H2 breath test: comparison with 14C-D-xylose and healthy controls," Am. J. Gastroenterology, Jul. 2005, 100(7):1566-1570.
Weems, "The Intestine as a Fluid Propelling System," Annu. Rev. Physiology, 1981, 43:9-19.
Yatsunenko et al., "Human gut microbiome viewed across age and geography," Nature, May 9, 2012, 486(7402):222-227.
Zoetendal et al., "The human small intestinal microbiota is driven by rapid uptake and conversion of simple carbohydrates," ISME Journal, Jan. 19, 2012, 6:1415-1426, 12 pages.

\* cited by examiner

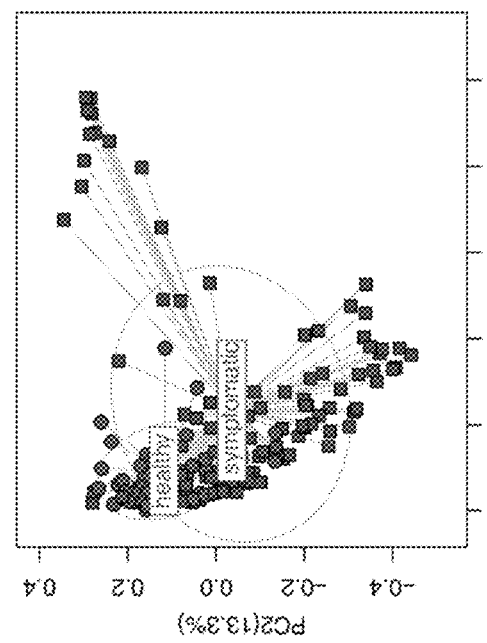
FIG. 1A
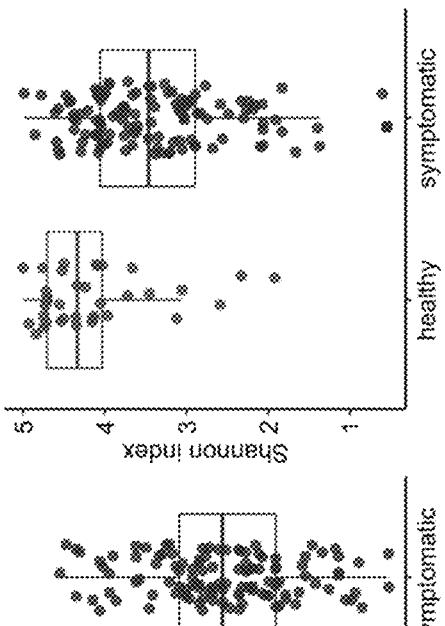
FIG. 1B
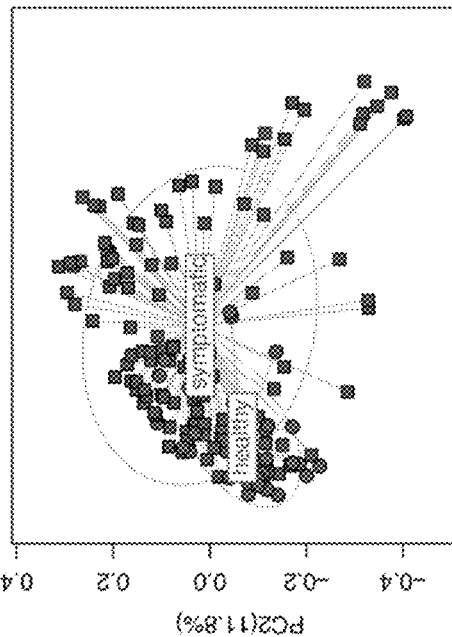
FIG. 1C
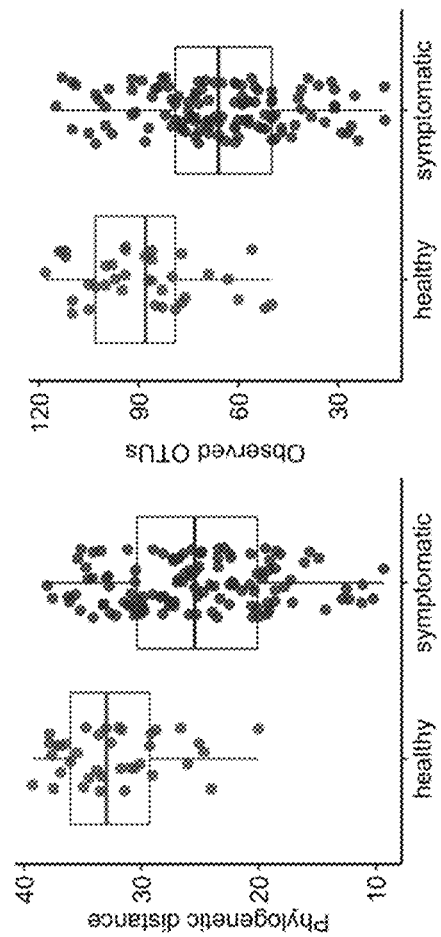
FIG. 1D
FIG. 1E

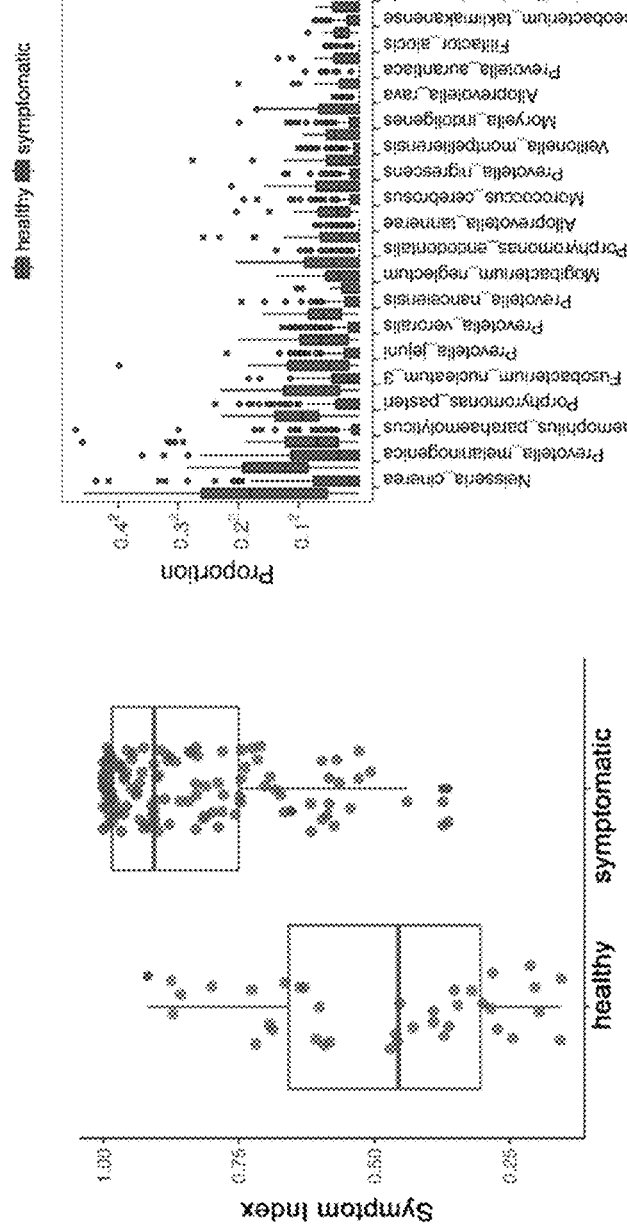
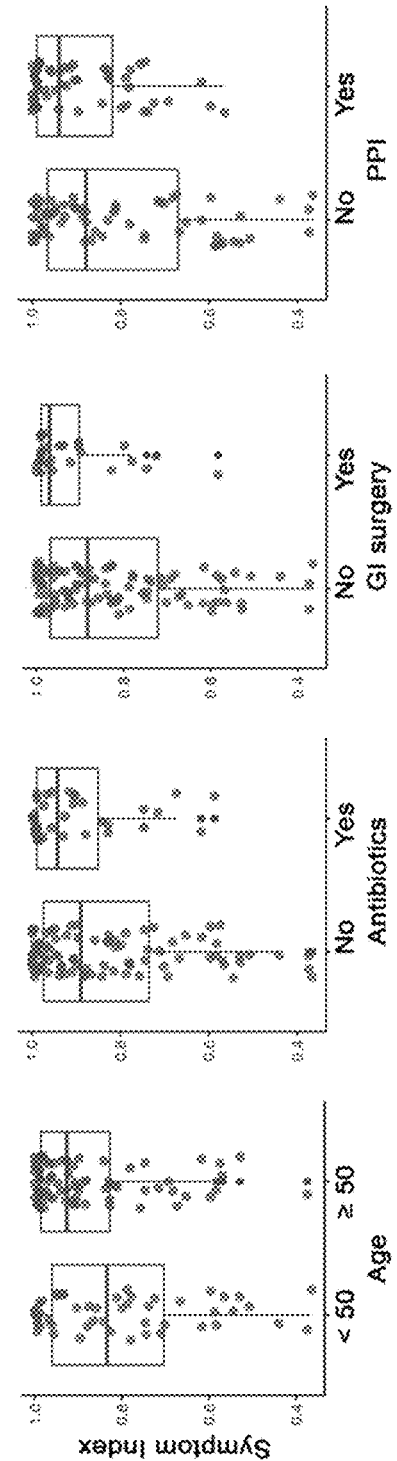
FIG. 3A  FIG. 3B  FIG. 3C  FIG. 3D  FIG. 3E  FIG. 3F

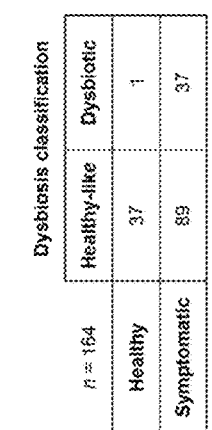
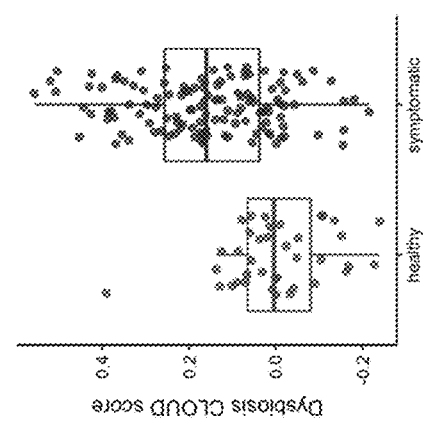
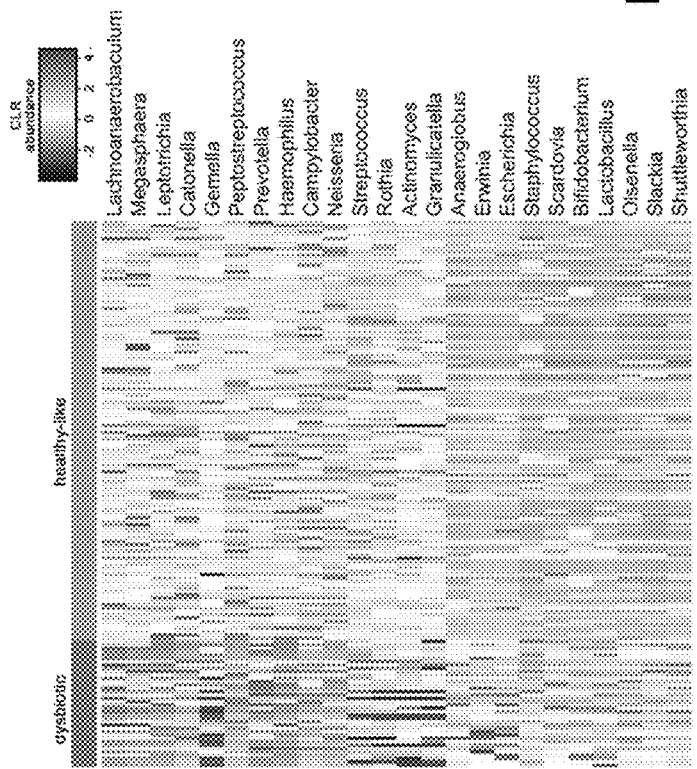
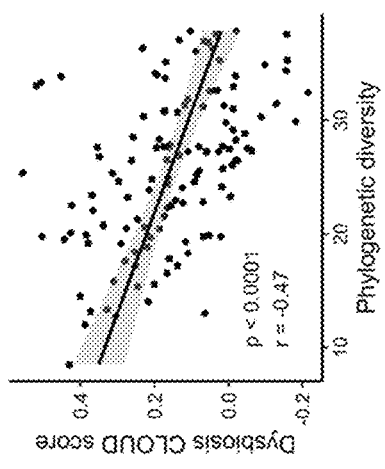
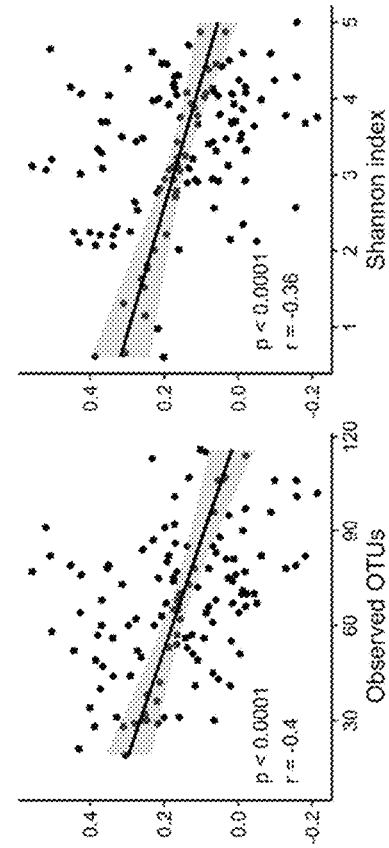
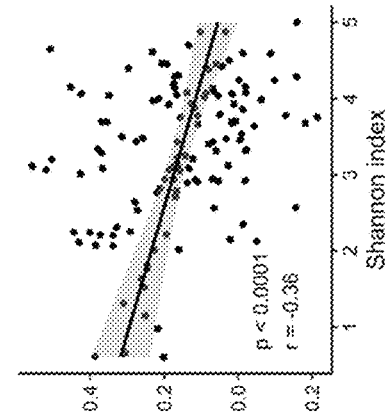
FIG. 4A
FIG. 4B
FIG. 4C
FIG. 4D
FIG. 4E
FIG. 4F

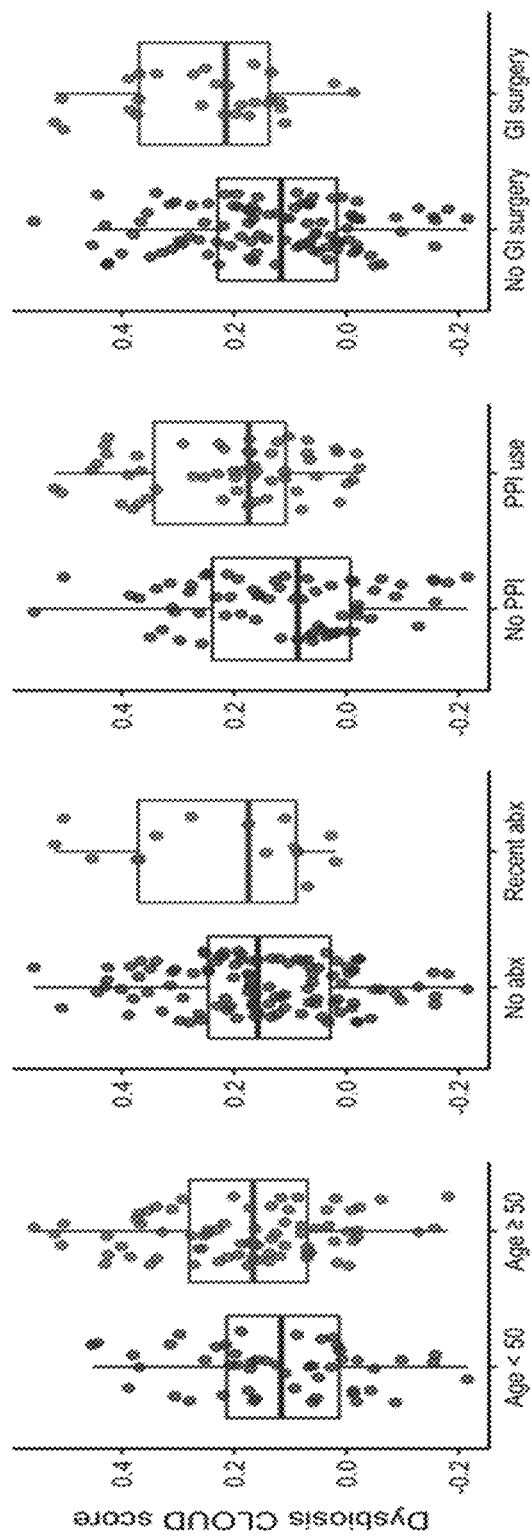

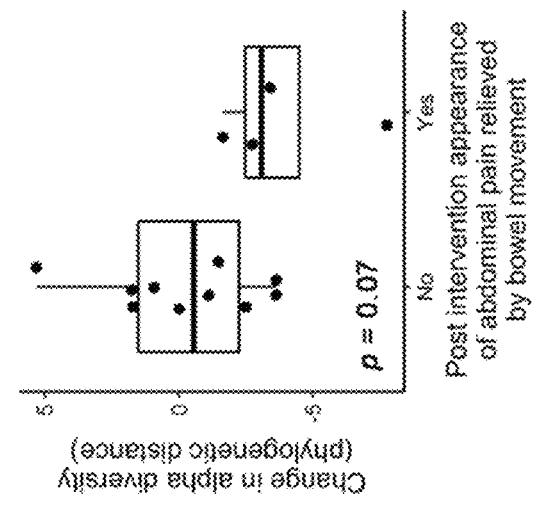
FIG. 11C
FIG. 11B
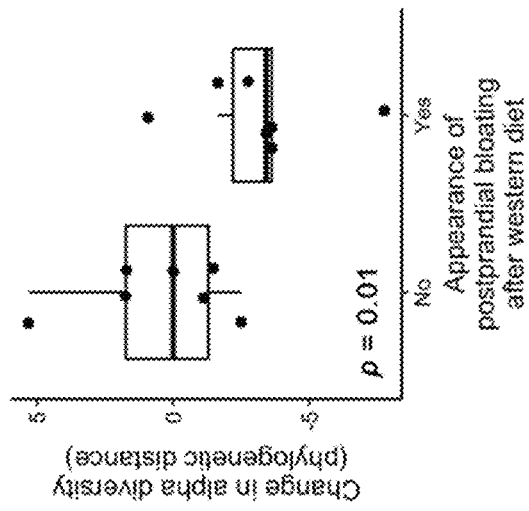
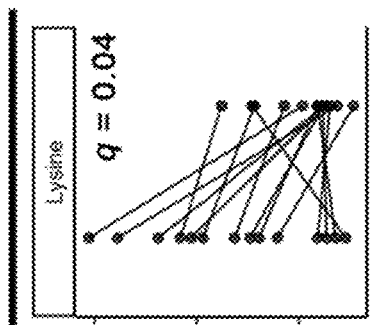
FIG. 11A
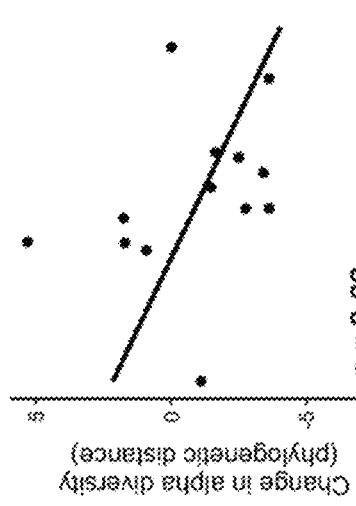
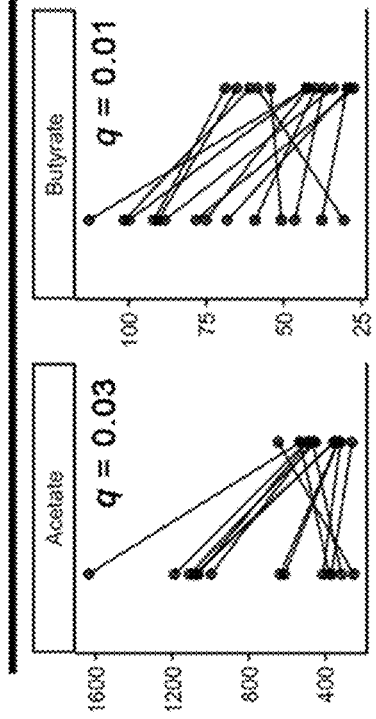
FIG. 11E
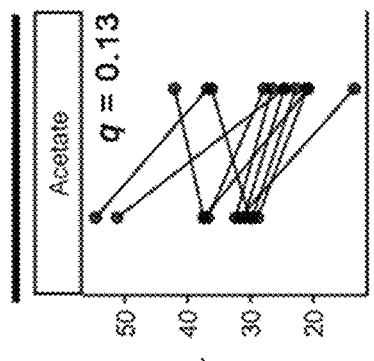
FIG. 11D

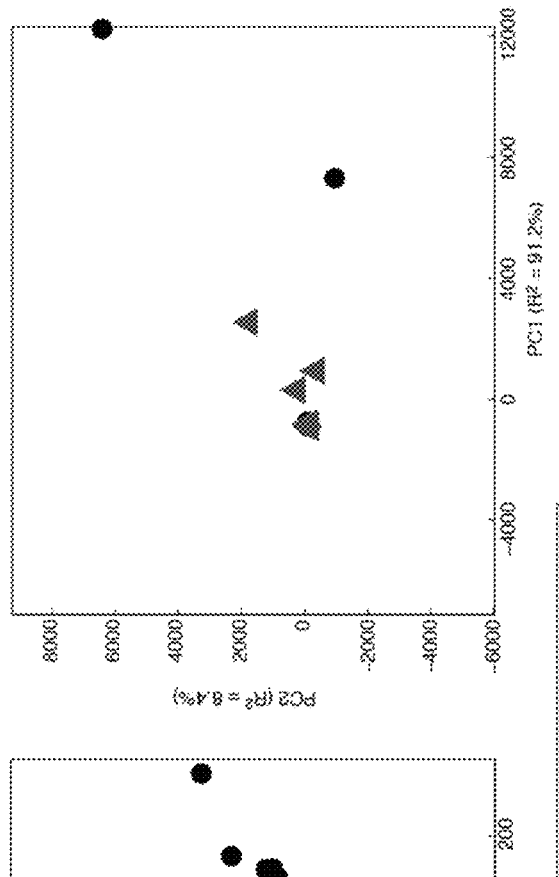
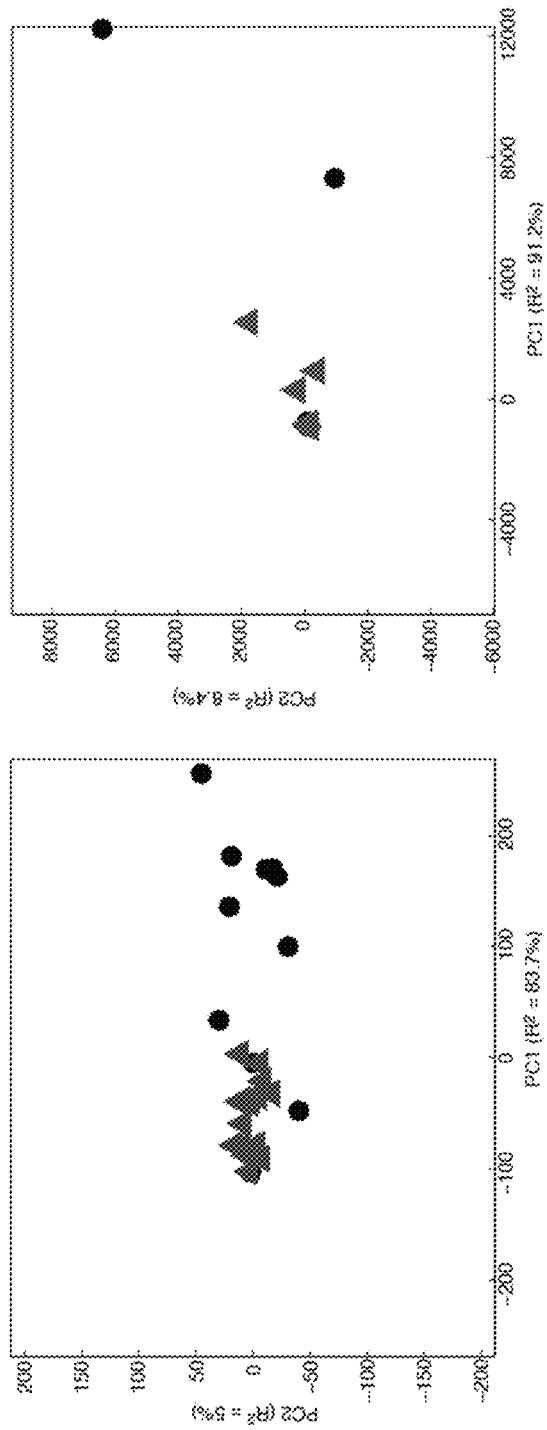
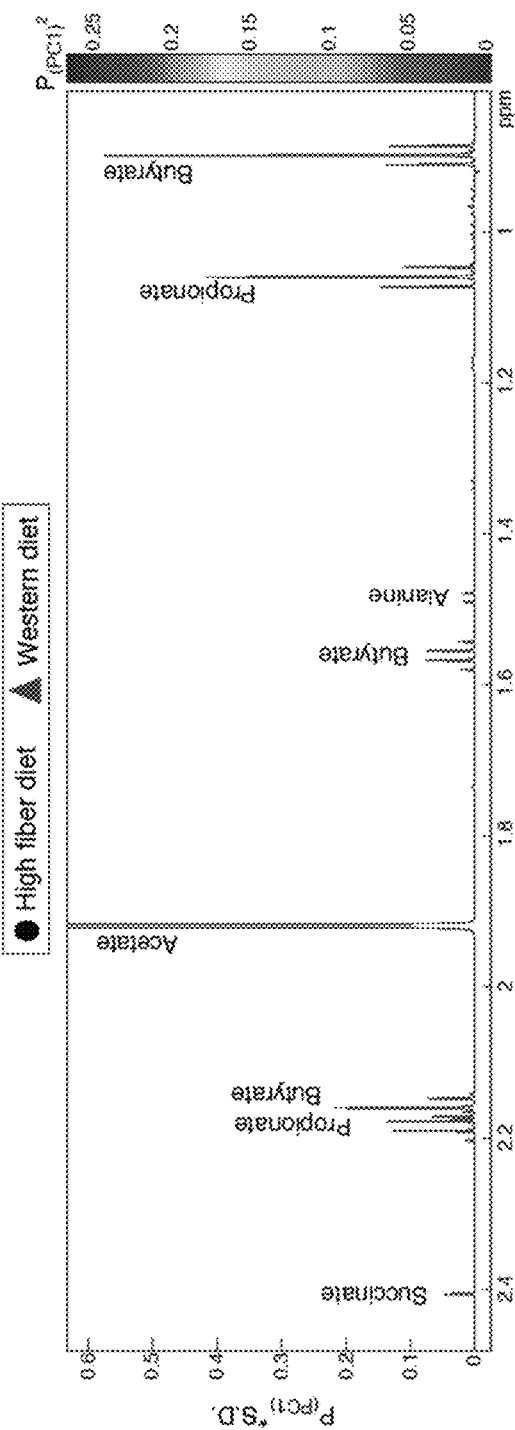

ASSESSING AND TREATING FUNCTIONAL GASTROINTESTINAL DISORDERS

CROSS-REFERENCE TO RELATED APPLICATIONS

This application claims the benefit of U.S. Patent Application Ser. No. 62/840,867, filed on Apr. 30, 2019. The disclosure of the prior application is considered part of (and is incorporated by reference in) the disclosure of this application.

BACKGROUND

1. Technical Field

This document relates to methods and materials involved in assessing and/or treating a mammal having a functional gastrointestinal disorder (FGID) such as irritable bowel syndrome (IBS). For example, methods and materials provided herein can be used for determining if a mammal having a FGID is likely to respond to a particular FGID treatment. This document also provides methods and materials for treating a mammal having a FGID.

2. Background Information

Small intestinal bacterial overgrowth (SIBO) has been implicated in driving gastrointestinal symptoms such as diarrhea, abdominal pain and bloating; the gold standard test for SIBO is a duodenal aspirate culture to measure microbial density in the duodenum (see, e.g., Corazza et al., *Gastroenterology* 98:302-309 (1990); King et al., *Gastroenterology* 91:1447-1451 (1986); and Bauer et al., *J. Hepatol.* 33:382-386 (2000)). SIBO is currently defined as $\geq 10^5$ CFU/mL on aspirate culture, based on the initial description in Billroth II anatomy patients with stagnant loop syndrome (King et al., *Gastroenterology* 76:1035-1055 (1979); Hamilton et al., *Q. J. Med.* 39:265-285 (1970); and Tabaqchali et al., *Proc. R. Soc. Med.* 59:1244-1246 (1966)). This has been extrapolated for the diagnosis of SIBO in other conditions. This approach to diagnosis is limited by the inability to differentiate disease-promoting microbes from potentially beneficial microbes and the inability to sample microbes in different regions of the small intestine. There is wide variability in antibiotic treatment response among patients diagnosed with SIBO, and in some cases antibiotic treatment can cause a worsening of GI symptoms (Maxwell et al., *Am. J. Gastroenterol.* 97:104-108 (2002)).

SUMMARY

SIBO has been implicated in symptoms associated with FGIDs. Characterizing the microbiota in a SIBO can be challenging due to the difficulty in accessing the small intestine and due to the lower microbial density that makes it difficult to obtain sufficient bacterial DNA (El Aidy et al., *Curr. Opin. Biotechnol.* 32:14-20 (2015)).

This document relates to methods and materials for assessing and/or treating mammals (e.g., humans) having a FGID (e.g., IBS). For example, methods and materials provided herein can be used for determining if a mammal having a FGID is likely to respond to a particular FGID treatment. In some cases, a small intestinal microbiome of a mammal having a FGID can be used to determine if that mammal is likely to respond to a particular FGID treatment. For example, a sample (e.g., a small intestine sample) obtained from a mammal having a FGID can be assessed to determine if the mammal is likely to respond to a particular FGID treatment based, at least in part, on the small intestinal microbiome of the sample. This document also provides methods and materials for treating a mammal having a FGID.

As demonstrated herein, SIBO based on duodenal aspirate culture reflects an overgrowth of anaerobes, does not correspond with small intestinal dysbiosis and patient symptoms, and may be a result of dietary preferences. Also as demonstrated herein, small intestinal microbiome is altered in symptomatic patients and does not correspond with aspirate culture results. The small intestinal microbiome in mammals (e.g., humans) with gastrointestinal symptoms can be used to select a targeted approach for treating that patient. For example, a mammal (e.g., a human) having a small intestinal microbiome including *Anaeroglobus* species, *Erwinia* species, *Escherichia* species, *Staphylococcus* species, *Scardovia* species, *Bifidobacterium* species, *Lactobacillus* species, *Olsenella* species, *Slackia* species, and *Shuttleworthia* species can be treated by administering one or more antibiotics (e.g., one or more narrow spectrum antibiotics) to the patient. For example, a patient having a small intestinal microbiome including *Anaeroglobus* species, *Erwinia* species, *Escherichia* species, *Staphylococcus* species, *Scardovia* species, *Bifidobacterium* species, *Lactobacillus* species, *Olsenella* species, *Slackia* species, and *Shuttleworthia* species, but having a reduced level of *Lachnoanaerobaculum* species, *Prevotella* species, *Leptotrichia* species, *Catonella* species, *Gemella* species, *Neisseria* species, *Haemophilus* species, and *Streptococcus* species can be treated by administering a composition containing one or more probiotics (e.g., one or more probiotics that are reduced or absent in the small intestinal microbiome of the patient) to the patient.

In general, one aspect of this document features methods for treating a mammal having a FGID. The methods can include, or consist essentially of, identifying a mammal having a FGID as having a small intestinal microbiome comprising two or more microbes selected from the group consisting of *Anaeroglobus* species, *Erwinia* species, *Escherichia* species, *Staphylococcus* species, *Scardovia* species, *Bifidobacterium* species, *Lactobacillus* species, *Olsenella* species, *Slackia* species, and *Shuttleworthia* species; and administering an antibiotic to the mammal. The mammal can be a human. The FGID can be IBS. The identifying step can include obtaining a sample from the small intestine of the mammal and determining the small intestinal microbiome within the sample. The sample can be a fecal sample or a duodenal aspirate sample. The antibiotic can be a narrow-spectrum antibiotic (e.g., tungsten, a phage therapy, Debio 1452, and a bacteriocin).

In another aspect, this document features methods for treating a FGID. The methods can include, or consist essentially of, administering an antibiotic to a mammal that has a FGID and that was identified as having a small intestinal microbiome comprising two or more microbes selected from the group consisting of *Anaeroglobus* species, *Erwinia* species, *Escherichia* species, *Staphylococcus* species, *Scardovia* species, *Bifidobacterium* species, *Lactobacillus* species, *Olsenella* species, *Slackia* species, and *Shuttleworthia* species. The mammal can be a human. The FGID can be IBS. The antibiotic can be a narrow-spectrum antibiotic (e.g., tungsten, a phage therapy, Debio 1452, and a bacteriocin).

In another aspect, this document features methods for treating a mammal having a FGID. The methods can include, or consist essentially of, identifying a mammal having a FGID as having a small intestinal microbiome comprising two or more microbes selected from the group consisting of *Anaeroglobus* species, *Erwinia* species, *Escherichia* species, *Staphylococcus* species, *Scardovia* species, *Bifidobacterium* species, *Lactobacillus* species, *Olsenella* species, *Slackia* species, and *Shuttleworthia* species; and comprising a reduced level of two or more microbes selected from the group consisting of *Lachnoanaerobaculum* species, *Prevotella* species, *Leptotrichia* species, *Catonella* species, *Gemella* species, *Neisseria* species, *Haemophilus* species, and *Streptococcus* species; and administering a probiotic to the mammal. The mammal can be a human. The FGID can be IBS. The identifying step can include obtaining a sample from the small intestine of the mammal and determining the small intestinal microbiome within the sample. The sample can be a fecal sample or a duodenal aspirate sample. The probiotic can be a *Lachnoanaerobaculum* species, *Megasphaera* species, *Leptotrichia* species, *Catonella* species, *Gemella* species, *Peptostreptococcus* species, *Prevotella* species, *Haemophilus* species, *Campylobacter* species, *Neisseria* species, *Streptococcus* species, *Rothia* species, *Actinomyces* species, or *Granulicatella* species.

In another aspect, this document features methods for treating a FGID. The methods can include, or consist essentially of, administering an antibiotic to a mammal that has a FGID and that was identified as having a small intestinal microbiome comprising two or more microbes selected from the group consisting of *Anaeroglobus* species, *Erwinia* species, *Escherichia* species, *Staphylococcus* species, *Scardovia* species, *Bifidobacterium* species, *Lactobacillus* species, *Olsenella* species, *Slackia* species, and *Shuttleworthia* species; and comprising a reduced level of two or more microbes selected from the group consisting of *Lachnoanaerobaculum* species, *Prevotella* species, *Leptotrichia* species, *Catonella* species, *Gemella* species, *Neisseria* species, *Haemophilus* species, and *Streptococcus* species. The mammal can be a human. The FGID can be IBS. The probiotic can be a *Lachnoanaerobaculum* species, *Megasphaera* species, *Leptotrichia* species, *Catonella* species, *Gemella* species, *Peptostreptococcus* species, *Prevotella* species, *Haemophilus* species, *Campylobacter* species, *Neisseria* species, *Streptococcus* species, *Rothia* species, *Actinomyces* species, or *Granulicatella* species.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIGS. 1A-1E contain data showing that the duodenal microbiome is significantly different in patients with GI symptoms. Principal coordinate axis (PCoA) plot showing beta diversity of patients with GI symptoms (n=126, blue) and healthy controls (n=38, red) based on unweighted UniFrac (FIG. 1A) and Bray-Curtis distances (FIG. 1B); p=0.001, PERMANOVA. Alpha diversity (within subject) of patients with GI symptoms (n=126, blue) and healthy controls (n=38, red) based on phylogenetic distance (FIG. 1C), observed OTUs (FIG. 1D), and Shannon diversity index (FIG. 1E) metrics (rarefied to 5,000 sequences; p<0.0001, t-test). Tukey boxplots show the median with IQR and 1.5 IQR whiskers.

FIGS. 3A-3F show that the symptom index differentiates healthy controls from patients with GI symptoms. FIG. 3A contains a symptom index indicating the probability (0 to 1) of being classified in the symptomatic patient group determined using Random Forests classification based on the individuals' OTU profiles. FIG. 3B contains Tukey boxplots show differences in relative abundance of the 26 OTUs among symptomatic patients (n=126, blue) and healthy controls (n=38, red) that significantly contribute to the Random Forest classification performance based on Boruta feature selection (boxplots show the median with IQR and 1.5 IQR whiskers). The four factors contributing to the variance in the symptom index among healthy controls (red) and symptomatic patients (blue) are Age (FIG. 3C), history of antibiotic use within 3 weeks history (FIG. 3D), GI surgery (FIG. 3E), and PPI (FIG. 3F).

FIGS. 4A-4F contain data showing that the dysbiosis index identifies a subset of symptomatic patients with altered microbial communities. FIG. 4A shows a classification of healthy and symptomatic patients as dysbiotic or healthy-like based on the CLOUD test which evaluates each sample by its distance to healthy controls' microbiome distribution. FIG. 4B shows a log-transformed CLOUD statistic for samples (or dysbiosis index (DI)) from healthy controls (n=38, red) and symptomatic patients (n=126, blue). Tukey boxplots show the median with IQR and 1.5 IQR whiskers. FIG. 4C contains a heatmap of significantly different genus level taxa from healthy control and symptomatic patients that contribute significantly to the DI identified using Boruta feature selection from the random forest model. Samples classified as dysbiotic or healthy-like are indicated at the top by orange and green, respectively. Pearson correlation of DI with alpha diversity based on phylogenetic diversity (FIG. 4D; p<0.0001, r=−0.47, Pearson correlation), observed OTUs (FIG. 4E; p<0.0001, r=−0.4, Pearson correlation), and Shannon index (FIG. 4F; p<0.0001, r=−0.36, Pearson correlation).

FIGS. 5A-5D contain data showing that host characteristics influence DI score. Differences in DI score (symptomatic patients and healthy controls) based on age (FIG. 5A), antibiotic use (FIG. 5B), PPI use (FIG. 5C), and history of gastrointestinal surgery (FIG. 5D).

FIG. 7A contains a PCoA plot showing beta diversity of patients with GI symptoms (n=126) based on Aitchison distance; ellipses represent 95% confidence intervals. Alpha diversity of symptomatic patients that tested SIBO positive (n=66) or negative (n=60) based on phylogenetic distance (FIG. 7B), observed OTUs (FIG. 7C), and Shannon metric (FIG. 7D); all p>0.05, t-test; rarefied to 5,000 sequences.

FIG. 8A) and pathway level (L2; FIG. 8B) imputed from microbiome in patients with GI symptoms (n=126) and healthy controls (n=38).

FIG. 10A contains a study design and dietary intervention in healthy individuals consuming high fiber diet. FIGS. 10B and 10C contain correlations between the within-individual microbial microbiome before and after intervention in duodenal aspirate (FIG. 10B) and stool (FIG. 10C) by Procrustes analysis (p=0.001, Monte Carlo simulation with 999 permutations).

FIGS. 11A-11E contain data showing that diet change is associated with change in host physiology, microbial diversity, and metabolites. FIG. 11A contains a Spearman correlation of change in alpha diversity (PD whole tree) and change in duodenal permeability measured by FITC flux across duodenal biopsy in an Ussing chamber (n=14, p=0.02, rho=-0.61, Spearman correlation). Association of change in alpha diversity (PD whole tree) with post-prandial bloating (FIG. 11B; n=14, p=0.01, Mann-Whitney test) and abdominal pain relieved by defecation (FIG. 11C; n=14, p=0.07, Mann-Whitney test). Tukey boxplots show the median with IQR and 1.5 IQR whiskers. Change in (D) acetate (n=11, FDR q=0.1, Wilcoxon signed rank test) in duodenal aspirates and (E) acetate (n=14, FDR q=0.03, Wilcoxon signed rank test), butyrate (n=14, FDR q=0.01, Wilcoxon signed rank test), and lysine (n=14, FDR q=0.04, Wilcoxon signed rank test) in stool measured before and after dietary intervention using $^1$H-NMR.

FIGS. 12A-12C contain data showing that dietary intervention impacts the metabolic profiles of fecal and duodenal samples. Cross-validated scores plots from the PCA models built on the fecal (FIG. 12A; $R^2$=88.7%) and duodenal samples (FIG. 12B; $R^2$=99.6%). FIG. 12C contains a back-scaled loadings plot for principal component 1 (PC1) from the PCA model comparing pre- and post-intervention fecal samples.

DETAILED DESCRIPTION

Figure 2:
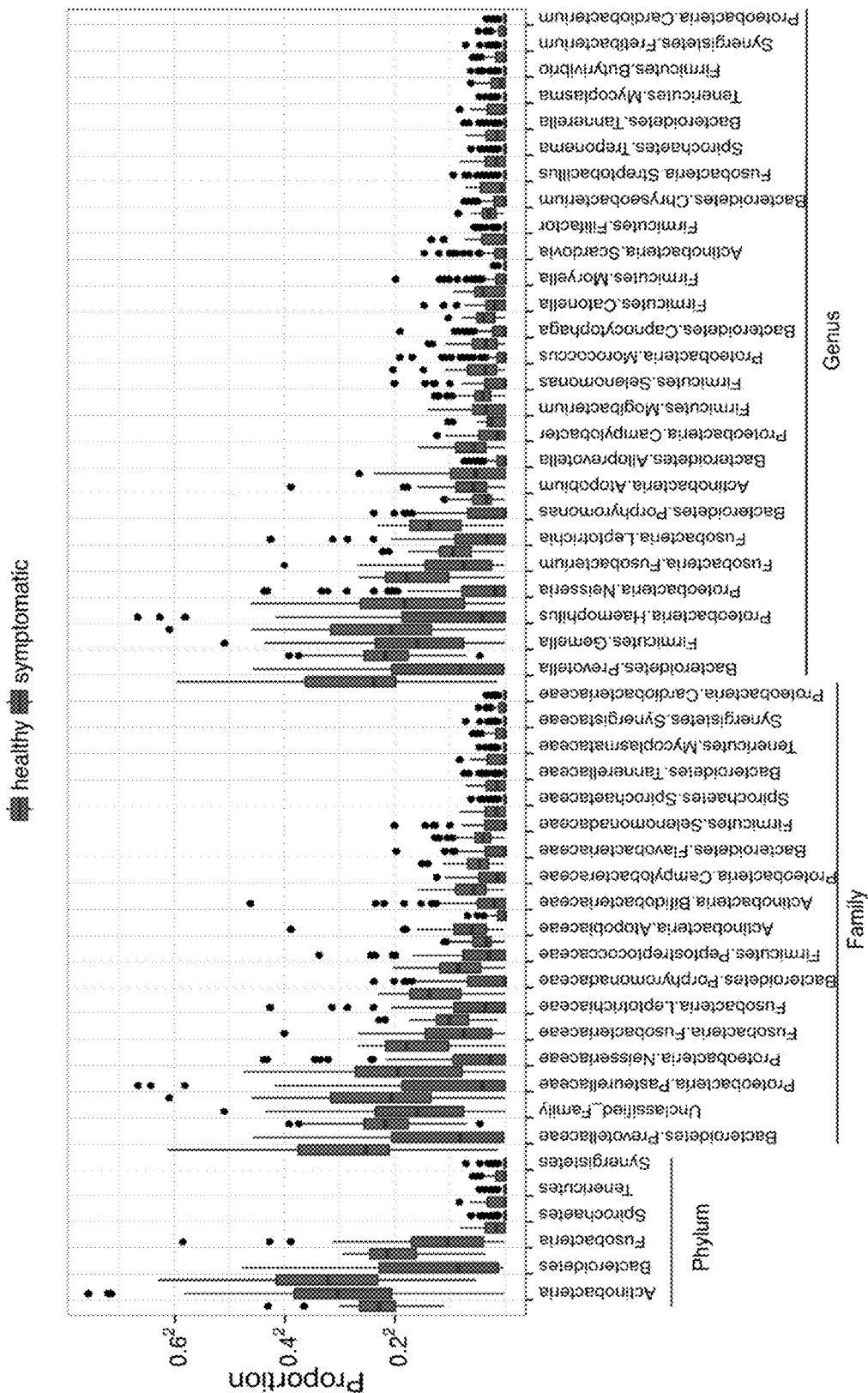
FIG. 2 contains data showing that small intestinal microbiome is significantly altered in symptomatic patients. Differences in relative abundances of microbial taxa at phylum, family, and genus levels among symptomatic patients and healthy controls (all FDR q<0.05).

This document provides methods and materials for assessing and/or treating mammals (e.g., humans) having a FGID (e.g., IBS). For example, methods and materials provided herein can be used to determine if a mammal having a FGID is likely to respond to a particular FGID treatment. In some cases, a small intestinal microbiome of a mammal having a FGID can be used to determine if that mammal is likely to respond to a particular FGID treatment. For example, a sample (e.g., a small intestine sample) obtained from a mammal having a FGID can be assessed to determine if the mammal is likely to respond to a particular FGID treatment based, at least in part, on the small intestinal microbiome of the sample. As described herein, a distinct small intestinal microbiome can be present in a mammal that is likely to respond to treatment with to one or more antibiotics, and a distinct small intestinal microbiome can be present in a mammal that is likely to respond to treatment with one or more probiotics. This document also provides methods and materials for treating a mammal having a FGID. For example, a treatment for a mammal having a FGID can be selected based, at least in part, on the small intestinal microbiome as described herein.

Any type of mammal can be assessed and/or treated as described herein. Examples of mammals that can be assessed and/or treated as described herein include, without limitation, primates (e.g., humans and monkeys), dogs, cats, horses, cows, pigs, sheep, rabbits, mice, and rats. A mammal can be any appropriate age. For example, a mammal can be an infant (e.g., can be a human from birth to about 2 years of age). For example, a mammal can be a juvenile (e.g., can be a human from about 2 years of age to about 17 years of age). For example, a mammal can be an adult (e.g., can be a human about 18 years of age or older). In some cases, the mammal can a human. In some cases, a mammal can have a SIBO. In some cases, a mammal having a FGID can be assessed for whether the mammal may be likely respond to a particular FGID treatment (e.g., based, at least in part, on the small intestinal microbiome of the mammal), and, optionally, can be treated with one or more FGID treatments as described herein.

A mammal having a FGID can have any type of FGID. As used herein, an FGID can include any disease or disorder that can include persistent and recurring gastrointestinal (GI) symptoms that occur as a result of abnormal functioning of the GI tract (e.g., abnormal motility of the GI tract, abnormal sensation of the GI tract, and/or brain-gut dysfunction of the GI tract). A FGID can affect any part of the GI tract (e.g., the esophagus, stomach, bile duct, and/or intestines). In some cases, a FGID can be a bowel disorder. In some cases, a FGID can be an esophageal disorder. In some cases, a FGID can be a gastroduodenal disorder. In some cases, a FGID can be a gallbladder disorder. In some cases, a FGID can be an anorectal disorder. Examples of FGIDs that can be assessed and/or treated as described herein include, without limitation, IBS (e.g., IBS with predominant constipation, IBS with predominant diarrhea, IBS with mixed bowel habits, and unclassified IBS), opioid-induced constipation, postprandial distress syndrome (PDS), epigastric pain syndrome (EPS), chronic nausea vomiting syndrome (CNVS), cyclic vomiting syndrome (CVS), cannabinoid hyperemesis syndrome (CHS), rumination syndrome, centrally mediated abdominal pain syndrome (CAPS), narcotic bowel syndrome (NBS), opioid-induced GI hyperalgesia, sphincter of Oddi disorders, levator ani syndrome, proctalgia fugax, aerophagia, dyschezia (e.g., infant dyschezia), and infant colic.

A FGID can include any appropriate GI symptoms. Examples of GI symptoms that can be exhibited by a mammal having a FGID include, without limitation, diarrhea, constipation, alternating between diarrhea and constipation, dyspepsia (indigestion), feeling of fullness, bloating, nausea, vomiting, abdominal pain, belching, chest pain, heartburn, reflux hypersensitivity, dysphagia, biliary pain, fecal incontinence, anorectal pain, defecatory propulsion, dyssynergic defecation, and regurgitation (e.g., infant regurgitation).

When treating a mammal (e.g., a human) having a FGID as described herein, the treatment can be effective to reduce the severity of one or more symptoms of the FGID. For example, a treatment described herein can be effective to reduce the severity of one or more symptoms in a mammal having a FGID by, for example, 10, 20, 30, 40, 50, 60, 70, 80, 90, 95, or more percent.

In some cases, a mammal that is assessed and/or treated as described herein can be identified as having a FGID. Any appropriate method can be used to identify a mammal as having a FGID. In some cases, a combination of symptoms and other factors (e.g., genetic factors such as the presence or absence of one or more polymorphisms, psychophysiological factors, sociocultural factors and family interactions, and environmental factors) can be used to identify a mammal as having a FGID. For example, when a mammal exhibits a combination of symptoms and other factors that meet a particular criteria (e.g., the Rome Criteria as described, for example, in Drossman, *Gastroenterology*, 150:1262-1279 (2016)), the mammal can be identified has having a FGID. In some cases, a mammal identified as having a FGID can have had x-rays, CT scans, blood tests, and/or endoscopic examinations having essentially normal/negative (non-disease) results.

Once identified as having a FGID, a mammal can be assessed to determine whether the mammal is likely to respond to a particular FGID treatment. For example, a sample (e.g., a small intestinal sample) obtained from the mammal having a FGID can be assessed to determine whether the mammal is likely to respond to a particular FGID treatment. As described herein, a sample obtained from a mammal having a FGID can be used to determine the small intestinal microbiome of the mammal, and can be used to determine whether the mammal is likely to respond to a particular FGID treatment.

Any appropriate sample from a mammal (e.g., a human) having a FGID can be assessed as described herein. In some cases, a sample can be a biological sample. For example, a sample can be a small intestinal sample. A sample can be a fresh sample or a fixed (e.g., frozen) sample. Examples of samples that can be assessed as described herein include, without limitation, fecal samples, fluid samples (e.g., small bowel aspirate samples such as duodenal aspirate samples), and tissue samples (e.g., small intestine tissue biopsies). For example, a fecal sample can be obtained from a mammal having a FGID and can be assessed to determine whether the mammal is likely to respond to a particular FGID treatment based, at least in part, on a small intestinal microbiome of the mammal. For example, a duodenal aspirate sample can be obtained from a mammal having a FGID and can be assessed to determine whether the mammal is likely to respond to a particular FGID treatment based, at least in part, on a small intestinal microbiome of the mammal.

A small intestinal microbiome described herein can include a panel of microbes. A panel of microbes can include any number of microbes. For example, a panel of microbes can include any two or more (e.g., two, three, four, five, six, seven, eight, nine, ten, or more) of the microbes described herein. A microbe in a small intestinal microbiome described herein can be any type of microbe. In some cases, a microbe can be gram-positive or gram-negative. A microbe can be aerobic or anaerobic. A microbe can belong to any appropriate phylum (e.g., Actinobacteria, Bacteroidetes, Fusobacteria, Tenericutes, and Synergistetes). A microbe can belong to any appropriate genus (e.g., *Lachnoanaerobaculum*, *Prevotella*, *Leptotrichia*, *Catonella*, *Gemella*, *Neisseria*, *Haemophilus*, and *Streptococcus*). Examples of microbes that can be present in a small intestinal microbiome described herein include, without limitation, *Lachnoanaerobaculum* species, *Megasphaera* species, *Leptotrichia* species, *Catonella* species, *Gemella* species, *Peptostreptococcus* species, *Prevotella* species (e.g., *P. melaninogenica*, *P. jejuni*, *P. veroralis*, *P. nanaceiensis*, *P. nigrescens*, *P. aurantiaca*, *P. pleuritidis*, and *P. shahii*), *Haemophilus* species (e.g., *H. parahaemolyticus*), *Campylobacter* species, *Neisseria* species (e.g., *N. cinerea*), *Streptococcus* species, *Rothia* species, *Actinomyces* species, *Granulicatella* species, *Anaeroglobus* species, *Erwinia* species, *Escherichia* species, *Staphylococcus* species, *Scardovia* species, *Bifidobacterium* species, *Lactobacillus* species, *Olsenella* species, *Slackia* species, *Shuttleworthia* species, *Porphyromonas* species (e.g., *P. pasteri*, *P. endodontalis*, and *P. cateoniae*), *Fusobacterium* species (e.g., *F. nucleatum*), *Mogibacterium* (e.g., *M. neglectum*), *Alloprevoltella* species (e.g., *A. tannerae*, and *A. cava*), *Morococcus* species (e.g., *M. cerebrosus*), *Veillonella* species (e.g., *V. montpelleirensis*), *Moryella* species (e.g., *M. indoligenes*), *Filifactor* species (e.g., *F. alocis*), *Chryseobacterium* species (e.g., *C. taklimakanense*), *Streptobacillus* species (e.g., *S. hongkonggensis*), *Treponema* species (e.g., *T. medium*), *Mycoplasma* species (e.g., *M. salivarium*), and *Butyrivibrio* species (e.g., *B. hungatei*) In some cases, microbes that can be present in a small intestinal microbiome described herein can be as described in Example 1. In some cases, microbes that can be present in a small intestinal microbiome described herein can be as shown in FIG. 2, FIG. 3, and/or FIG. 4. In some cases, microbes that can be present in a small intestinal microbiome described herein can be as shown in Table 2.

Any appropriate method can be used to identify the presence or absence of one or more microbes described herein (e.g., one or more microbes in a small intestinal microbiome described herein). For example, 16S rRNA-based techniques, next-generation sequencing, shotgun metagenomics, and fluorescence in situ hybridization can be used to identify the presence or absence of one or more microbes. In some cases, one or more microbes can be identified as described in Example 1.

Once the small intestinal microbiome of a mammal having a FGID has been identified, a treatment option for the mammal can be selected. As described herein, the small intestinal microbiome present in a mammal having a FGID can be used to determine whether that mammal is likely to respond to a particular FGID treatment. A FGID treatment can be any appropriate FGID treatment. Examples of FGID treatments include, without limitation, administering one or more antibiotics, administering one or more probiotics, altering the mammal's diet (e.g., reducing the amount of fiber in the mammal's diet and/or increasing the amount of simple sugar in the mammal's diet), antispasmodics (e.g., dicyclomines such as BENTYL®, and hyoscyamines such as LEVSIN®), pro-motility agents (e.g., tegaserod maleates such as ZELNORM®), anti-diarrheals (e.g., diphenoxylate/ atropines such as) LOMOTIL®), laxatives (e.g., polyethylene glycols such as MiraLAX), and antidepressants.

In some cases, a mammal can be identified as being likely to be responsive to one or more antibiotics based, at least in part, on the small intestinal microbiome of the mammal. For example, a mammal having a FGID can be identified as being likely to be responsive to one or more antibiotics based, at least in part, on the presence of a small intestinal microbiome that includes two or more (e.g., two, three, four, five, six, seven, eight, nine, ten, or more) of *Anaeroglobus* species, *Erwinia* species, *Escherichia* species, *Staphylococcus* species, *Scardovia* species, *Bifidobacterium* species, *Lactobacillus* species, *Olsenella* species, *Slackia* species, and *Shuttleworthia* species. In some cases, when a mammal having a FGID is identified as being likely to respond to one or more antibiotics, the mammal can be administered or instructed to self-administer one or more antibiotics to treat the mammal.

When a mammal having a FGID is identified as being likely to respond to one or more antibiotics as described herein (e.g., based, at least in part, on the small intestinal microbiome of the mammal having FGID), the mammal can be administered or instructed to self-administer one or more antibiotics. For example, a mammal having a FGID can be administered one or more antibiotics that target one or more microbes present in the small intestinal microbiome of the mammal. An antibiotic can be any appropriate antibiotic. In some cases, an antibiotic can be a broad-spectrum antibiotic. Examples of broad-spectrum antibiotics that can be used as described herein include, without limitation, imipenem, cephalosporins (e.g., ceftazidime), fluoroquinolones (e.g., ofloxacin, levofloxacin, and ciprofloxacin), and rifaximin In some cases, an antibiotic can be a narrow spectrum (e.g., targeted) antibiotic. Examples of narrow-spectrum antibiotics include, without limitation, tungsten (e.g., sodium tungstate; targeting enterobacteriaceae), phage therapy (targeting *Anaeroglobus, erwinia, Escherichia, staphylococcus, scardovia, slackia*, shuttelworthia, and/or *olsenella*), Debio 1452 (targeting *staphylococcus*), and bacteriocins (targeting *Anaeroglobus, erwinia, Escherichia, staphylococcus, scardovia, slackia*, shuttelworthia, and/or *olsenella*). For example, when a mammal having a FGID is identified as having a small intestinal microbiome that includes one or more *Staphylococcus* species, the mammal can be administered Debio 1452 to treat the mammal. In cases where a mammal having a FGID is treated by administering two or more antibiotics (e.g., two or more narrow-spectrum antibiotics), the two or more antibiotics can be administered at the same time or independently. For example, a first antibiotic described herein can be administered first, and a second antibiotic described herein can be administered second.

In some cases, a mammal can be identified as being likely to be responsive to one or more probiotics based, at least in part, on the small intestinal microbiome of the mammal. For example, a mammal having a FGID can be identified as being likely to be responsive to one or more probiotics based, at least in part, on the presence of a small intestinal microbiome that includes two or more (e.g., two, three, four, five, six, seven, eight, nine, ten, or more) of *Anaeroglobus* species, *Erwinia* species, *Escherichia* species, *Staphylococcus* species, *Scardovia* species, *Bifidobacterium* species, *Lactobacillus* species, *Olsenella* species, *Slackia* species, and *Shuttleworthia* species; and a small intestinal microbiome that includes a reduced level or an absence of two or more (e.g., two, three, four, five, six, seven, eight, nine, ten, or more) of *Lachnoanaerobaculum* species, *Prevotella* species, *Leptotrichia* species, *Catonella* species, *Gemella* species, *Neisseria* species, *Haemophilus* species, and *Streptococcus* species. A reduced level of a microbe refers to any level of the microbe that is lower than the median level of that microbe typically observed in a sample (e.g., a control sample) from one or more healthy mammals (e.g., healthy humans and mammals that do not have a FGID). An eliminated level of a microbe refers to any non-detectable level of that microbe. In some cases, when a mammal having a FGID is identified as being likely to respond to one or more probiotics, the mammal can be administered or instructed to self-administer one or more probiotics to treat the mammal.

When a mammal having a FGID is identified as being likely to respond to one or more probiotics as described herein (e.g., based, at least in part, on the small intestinal microbiome of the mammal having FGID), the mammal can be administered or instructed to self-administer one or more probiotics. For example, a mammal having a FGID can be administered one or more probiotics that include one or more microbes not present in the small intestinal microbiome of the mammal, or that are present in the small intestinal microbiome of the mammal in reduced levels (e.g., as compared to the level present in a mammal that does not have a FGID). Examples of probiotics include, without limitation, *Lachnoanaerobaculum* species, *Megasphaera* species, *Leptotrichia* species, *Catonella* species, *Gemella* species, *Peptostreptococcus* species, *Prevotella* species (e.g., *P. melaninogenica, P. jejuni, P. veroralis, P. nanaceiensis, P. nigrescens, P. aurantiaca, P. pleuritidis*, and *P. shahii*), *Haemophilus* species (e.g., *H. parahaemolyticus*), *Campylobacter* species, *Neisseria* species (e.g., *N. cinerea*), *Streptococcus* species, *Rothia* species, *Actinomyces* species, and *Granulicatella* species. For example, when a small intestinal microbiome of a mammal having a FGID does not include, or includes reduced levels of, one or more *Lachnoanaerobaculum* species, the mammal can be administered one or more *Lachnoanaerobaculum* species to treat the mammal.

The invention will be further described in the following examples, which do not limit the scope of the invention described in the claims.

EXAMPLES

Example 1: Small Intestinal Microbial Dysbiosis Underlies Symptoms Associated with Functional Gastrointestinal Disorders The small intestinal microbiota of patients with gastrointestinal symptoms undergoing testing for SIBO were characterized. A significant alteration in the small intestinal microbiome was found, especially in a subset of symptomatic patients. The alteration indicated potential consequences for the functional capacity of the small intestinal microbiome specifically with regard to processing of dietary carbohydrate and fiber. SIBO however did not correlate with patient symptoms and was also seen in healthy individuals consuming a high fiber diet. In healthy individuals consuming a high fiber diet, it was found that a short term switch to low fiber diet leads to change in intestinal permeability and appearance of gastrointestinal symptoms associated with a change in microbial diversity. These findings suggest that characterizing the small intestinal microbiome is important as it may allow a more targeted antibiotic approach in symptomatic patients. At the same time relying on quantitative culture of small intestinal aspirates alone may not sufficient as these results may be influenced by diet.

Methods:

Ethical Approval of Human Studies

All human studies were approved by the Mayo Clinic IRB [test samples (16-006388 and 15-003235), healthy controls (14-002382 and 15-003603)] and complied with all relevant ethical regulations. The dietary intervention study was registered with ClinicalTrials.gov (NCT03266536). All subjects in the dietary study provided informed consent while the small bowel aspirates were obtained from clinical microbiology laboratory under a consent waiver from the IRB for protocol 15-003235.

Collection of Small Intestinal Aspirates

Consecutive small bowel aspirate samples from symptomatic patients following diagnostic esophagogastroduodenoscopy (EGD) were obtained directly from the microbiology laboratory. Duodenal aspirate samples were collected during EGD following direct passage to the duodenum with minimal inflation in the stomach using a standard single lumen aspiration catheter passed through the suction port of the endoscope. Samples associated with patients who previously provided consent allowing for review of electronic medical record were included. A total of 143 aspirates from symptomatic patients were obtained over this time interval. After excluding samples due to lack of consent or low read depth on sequencing (<1,000) a total of 126 symptomatic patients was included. Duodenal aspirates obtained from 38 healthy volunteers participating in other research studies and collected in a similar manner were also obtained and processed similarly. Clinical metadata was obtained by retrospective review of electronic medical record including demographic information, body mass index (BMI), clinical indication for SIBO testing, quantitative aerobic and anaerobic aspirate culture results, antibiotic course for treatment of SIBO, clinical response to antibiotics, need for repeat antibiotics, recent medications including antibiotics and proton pump inhibitor use, gastrointestinal surgeries, comorbid conditions etc.

Criteria for Diagnosis of SIBO Based on Quantitative Cultures

Small bowel aspirates (10 µl) were streaked on RBAP (blood agar), REMB (gram negative selection media), RBAPA (Pre-reduced blood agar) and incubated aerobically at 35° C., 5% $CO_2$, RIMA (yeast selective media) and incubated at room temperature and on RCDC (anaerobic blood agar), RLKC (Laked blood Kanamycin Vancomycin—*Prevotella* selection), RPEA (phenol alcohol agar-gram positive selective) and incubated anaerobically either in the clinical laboratory or research laboratory. Total bacteria (anaerobic plus aerobic counts) were reported as less than or greater than $10^5$ CFU/ml, and the diagnosis of small intestinal bacterial overgrowth (SIBO) was based on duodenal aspirate culture demonstrating ≥$10^5$ CFU/mL bacterial growth (aerobic, anaerobic, or both) over 48 hours.

Comparison of Cultures and 16S rRNA Sequencing

Bacterial DNA was extracted from aspirates and duodenal biopsies using phenol-chloroform, and from stool using a MoBio fecal DNA extraction kit, followed by 16S rRNA amplification using Nextera library compatible primers flanking the V4 hypervariable region ([forward overhang]+ 515F: [TCGTCGGCAGCGTCAGATGTGTATAAGA-GACAG]GTGCCAGCMGCCGCGGTAA (SEQ ID NO:1); and [reverse overhang]+806R: [GTCTCGTGGGCTCG-GAGATGTGTATAAGAGACAG]GGACTACHVGGGT WTCTAA T (SEQ ID NO:2)) and prepared for sequencing using a dual-indexing protocol. All samples were sequenced together in 2×300 paired-end mode on an Illumina Mi Seq instrument using v3 reagents by the University of Minnesota Genomics Center.

Raw paired-end sequences were quality-filtered, adapter-trimmed, and stitched using the quality control pipeline SHI7, with a trim threshold >32 and mean quality score >35. Preprocessed reads were analyzed by closed reference picking with the accelerated optimal gapped alignment engine BURST in CAPITALIST mode against the NCBI RefSeq Targeted Loci Project bacterial and archaeal 16S databases at 97 percent identity. After filtering for samples with low read depth, analysis of 126 symptomatic patients and 38 healthy controls was performed. Diversity analyses were done using QIIME v1.9.1, and other data analyses, statistical tests, and visualizations were performed in R. To compare diversity of different GI tract sample types in the dietary intervention study, sequences were rarefied to the median depth of the site with the fewest reads, CLR-transformed after multiplicative replacement, and analyzed with custom R scripts and the "vegan" package.

Differential abundance analysis between the healthy and symptomatic subjects was performed on normalized abundance data at each taxonomic rank using a permutation test (1,000 permutations) with t-statistic as the test statistic. Square-root transformation was applied to the normalized abundance data before testing. Taxa with prevalence <10% or the maximum proportion <0.2% were excluded from testing. False discovery rate (FDR) control (Benjamini-Hochberg procedure) was performed at each taxonomic rank to correct for multiple testing. The symptom index was generated using random forests classification based on the normalized OTU-level data ("randomForest" package in R). The index scale was defined as the out-of-bag probability of symptomatic patient classification based on the generated model. This method prevents overtraining by holding out the sample to be classified and predicting based on the remaining n-1 dataset. Boruta feature selection ("Boruta" package in R) was used to identify OTUs that contribute significantly to the classification. Associations with the seven demographic or clinical variables were tested using linear regression models and corrected for multiple testing using FDR control.

The dysbiosis index was generated using the CLOUD method as described elsewhere (see, e.g., Montassier et al., *Microbiome* 6:137 (2018)). Briefly, the Aitchison distance matrix of healthy samples was used as a reference cloud, and the distance of each healthy sample to the healthy cloud was calculated for every sample in the dataset. This distance calculation was then repeated for each symptomatic patient sample relative to the healthy cloud; distances greater than 2 standard deviations (SD) from the healthy distance mean are considered "dysbiotic"; those within 2 SD of the healthy distance mean are considered "healthy-like". This CLOUD dysbiosis score was then validated using an orthogonal approach based on the SI scores: the healthy SI scores were fit to a logit scale distribution (healthy control SI values are approximately normal on logit scale; p=0.41, Shapiro-Wilk normality test). The 2-SD rule was again applied, classifying samples greater than 2 SD from the mean of the healthy distribution as "dysbiotic" and those within 2 SD as "healthy-like." To generate a dysbiosis index here, the samples were then re-classified by random forest using the new group classifications, and used the OOB probability of "dysbiotic" classification as the index score. These two independent methods are in close agreement, as evaluated by the high degree of correlation between the samples' CLOUD dysbiosis scores and their probability-based index score ($r=0.7$, $p=2\times10^{-16}$, Pearson correlation). The CLOUD distance score was used in all subsequent analyses. As a comparison, the data were also grouped using spectral clustering, as implemented in the R package "kernlab" v0.9.27, using two cluster centers and default settings as described elsewhere (see, e.g., Karatzoglou et al., *J. Statist. Software*, doi: 10.18637/jss.v011.i09 (2004)).

Imputed Functions from Microbiota Composition

To predict microbial functions, preprocessed DNA reads were aligned to the GreenGenes 16S rRNA database version 13_8 using BURST at 97 percent identity. The resulting OTU tables were used to generate predicted KEGG annotations using PICRUSt v1.1.3. Linear discriminant analysis (LDA) effect size (LEfSe; Galaxy Version 1.0) was then used to identify putative functions that differed significantly (LDA score >2.0) between groups.

Dietary Intervention Study in Healthy Volunteers

This was a single-center dietary intervention study in healthy volunteers consuming a high fiber diet at baseline. The study was registered with clinicaltrials.gov under NCT03266536. Eligible subjects were healthy adults ($\geq 18$ years) with baseline fiber intake $\geq 11$ g/1000 calories/day; <10% daily calories from added sugar; $\geq 5$ servings of fruits and vegetables/day; and $\leq 13\%$ daily calories from saturated fat based on completed food frequency questionnaire. Patients were excluded from the study if they did not meet the above diet requirements, had a known diagnosis of inflammatory bowel disease, microscopic colitis, celiac disease or other inflammatory conditions, presence of abdominal symptoms based on baseline questionnaire, oral antibiotic or probiotic use within the past 4 weeks, pregnancy or plans to become pregnant within the study time frame, or any other disease(s), condition(s) or habit(s) that would interfere with completion of study. Dietary instructions and food choices were discussed at the index, pre-intervention visit by a licensed dietician.

All subjects were screened in person or by phone and completed a food frequency questionnaire to ensure they met inclusion and exclusion criteria. At the initial and follow up visit they underwent EGD with conscious sedation. Duodenal aspirates were obtained via a standard suction catheter passed through the suction port with minimal inflation in the stomach; an aliquot was submitted to clinical laboratory for testing for SIBO and the remaining was stored for microbiome analysis at −80° C. Eight duodenal biopsies were obtained for Ussing chamber studies, microbiome analysis and host RNA seq. At initial and follow up visits, participants completed a symptom and demographic questionnaire and provided a stool sample. Symptoms assessed on questionnaires included: stool frequency, straining, incomplete evacuation, hard/lumpy stools, abdominal pain associated with bowel movements, diarrhea/loose-watery stools, bloating, swallowing difficulties, nausea/vomiting, heartburn, fatigue, and appetite. Answers were recorded in a binary (yes/no) fashion. For the intervention, all participants consumed a 7-day standardized diet with typical United States macronutrient calorie distribution: 50% from carbohydrates, 35% from fats, and 15% from protein. The diet was low in fiber (<10 g/1000 calories/day) and high in simple sugar ($\geq 50\%$ of daily carbohydrates).

Statistical Power Analysis

Post-hoc power calculation was performed for the comparison of the microbiome between healthy and symptomatic subjects, focusing on the power of differential abundance analysis, where there was much lower statistical power compared to alpha- and beta-diversity analyses, due to multiple testing correction. The web-based microbiome power calculator was used to conduct power analysis (fedematt.shinyapps.io/shinyMB/), which was based on Monte Carlo simulations and Wilcoxon-Mann-Whitney (WMW) test. A false discovery rate of 5% was used to correct for multiple testing. Assuming that testing was of 65 genera with the abundance of 10 moderately abundant genera (abundance rank 6-15) decreasing by 50% in symptomatic patients (compared to 26 differential genera with a median decrease by 59% in the observed data), an average power of 75% was used to detect these 10 differential genera and a power of 100% to detect at least one significant genus at current sample size. Therefore, the study was reasonably powered to detect a moderate taxa difference when comparing the healthy and symptomatic subjects.

Ex Vivo Epithelial Barrier Function

Ussing chamber studies were performed to measure duodenal mucosal barrier function and secretory responses as described elsewhere (see, e.g., Peters et al., *Am J Gastroenterol* 112:913-923 (2017)). Briefly, duodenal biopsies were mounted in 4 ml Ussing chambers (Physiologic Instruments, San Diego, CA) exposing 0.031 $cm^2$ area, within 45 minutes of collection. Chambers were filled with Krebs with 10 mM mannitol (mucosal side) and Krebs with 10 mM glucose (submucosal side). Baseline transepithelial resistance (TER) and short circuit current (Isc) of each tissue was measured using a pair of Ag/AgCl electrodes with agar-salt bridges and a pair of current-giving platinum electrodes to maintain voltage clamp conditions. Paracellular flux across biopsies was measured using 4 kDa FITC-dextran administered on the mucosal side (1 mg/ml chamber concentration). Sampling was done from the submucosal side every 30 minutes for a total of 3 hours and cumulative fluorescence was measured using a Synergy Multi-Mode Microplate Reader (BioTek, VT) and converted to concentration using standard curves. Cumulative flux at the end of 3 hours was calculated for FITC-dextran. Spearman correlations (nonparametric) were used to test for a relationship between the microbiome diversity and FITC-dextran flux.

RNA Seq

Biopsy samples were thawed on ice, homogenized and centrifuged at 13,000 RPM, and the supernatant was transferred to a new tube. RNA was prepared using the RNeasy Mini Kit (QIAGEN, Hilden, Germany) and sequenced on an Illumina HiSeq 2500. Data analysis was done using Mayo Analysis Pipeline for RNA Sequencing (MAP-RSeq) with alignment to the human genome build (GRCh38.78). Briefly, the MAP-RSeq pipeline preforms quality assessment of sequence reads from a FASTQ file, aligns the remaining the remaining reads with TopHat, and gene counts are aggregated with the Python HTSeq library. Average total read depth was 57,052,595 (Standard deviation of $8.5\times 10^1\backslash 6$) and on average 87.0% (Standard deviation of 2.0%) of the total reads mapped to gene models. Conditional quantile normalization was performed to account for gene length and GC content biases.

$^1$H NMR Metabolomics Sample Preparation

Aspirate samples were centrifuged at 4° C. at 12,000×g for 5 minutes. 162 µL of the supernatant was mixed with 18 µL of NMR buffer (1.5M $KH_2PO_4$, 1 g/L of TSP and 0.13 g/L of $NaN_3$, Sigma-Aldrich) and transferred to a 3 mm NMR tube. Fecal samples were pre-weighed (~100 mg), randomised, and emptied into a screw-cap tube containing 50 mg of 1.0 mm Zirconia beads, to which 400 µL of ACN:H$_2$O (1:3) was added. The tube was placed in a Biospec bead beater for 30 seconds. The homogenized sample was then centrifuged for 20 minutes at 16,000×g. The supernatant was carefully transferred into spin filter tubes and centrifuged for 30 minutes at 16,000×g. 80 µL of the filtered fecal water was aliquoted into a 96 well plate, and 10 µL were used for quality control. Filtered fecal water in the 96 well plate was dried down under nitrogen flow before reconstituting with 540 µL of D$_2$O (Sigma-Aldrich) and 60 µL of the NMR buffer. The reconstituted fecal water and buffer mixture was transferred to 5 mm NMR experiment tubes.

$^1$H NMR Experiment

Metabolic profiles were measured on a Bruker 600 MHz spectrometer (Bruker Biospin, Rheinstetten, Germany) set at a constant temperature of 300 K for urine, aspirate and fecal samples and 310 K for plasma samples. A standard one-dimensional NOSEY experiment was performed for each urine, aspirate and fecal water sample and CPMG experiment for plasma samples. A total of 64 scans were acquired per sample into 64 K data points for urine, aspirates and plasma; 128 scans per sample were collected into 64 K data points for fecal water.

$^1$H NMR Data Pre-Processing

The spectra data were imported into MATLAB (Version 8.3.0.532 R2014a, Mathworks Inc, Natick, MA, USA). A series of in-house developed scripts was used for the following executions. Phasing, baseline corrections and spectral calibration to TSP (0 ppm). The spectra were manually aligned. In order to account for the difference in sample concentration, probabilistic quotient normalization was applied to the samples. In-house scripts were used to construct PCA and OPLS-DA models and integrate peaks of interest. Feature correlations and trends were analyzed in R.

Code Availability

Previously published software packages and versions used to analyze microbiome, metabolomics, and RNAseq data are cited in the methods above. R code used for bioinformatic processing of the microbiome data and construction of the symptomatic and dysbiosis indices is available on GitHub (github.com/RRShieldsCutler/small bowel dysbiosis/).

Data and Materials Availability

All 16S rRNA gene amplicon data and associated metadata that support the findings of this study are available through the European Nucleotide Archive (ENA) with accession codes PRJEB31438 (ebi.ac.uk/ena/data/view/PR-JEB31438) and PRJEB31439 (ebi.ac.uk/ena/data/view/PR-JEB31439). Metabolomics data available through the EMBL-EBI MetaboLights database with the accession code MTBLS876 (ebi.ac.uk/metabolights/MTBLS876), RNAseq data are available at GEO database under accession number GSE128189 (ncbi.nlm.nih.gov/geo/query/acc.cgi?acc=GSE128189). Patient derived biological materials cannot be shared based on protocol approved by institutional IRB.

Results:

Duodenal Aspirate Cultures do not Correlate with Patient Symptoms 126 symptomatic (21% male; age 15-89 years, median 55 years) patients who underwent esophagogastroduodenoscopy (EGD) with duodenal aspirate collection were evaluated; the major symptoms that led to investigation of small bowel bacterial counts included diarrhea (45%), abdominal pain (28%), and bloating (13%). A concomitant organic diagnosis was only noted in a minority of patients and included celiac disease (n=14), microscopic colitis (n=6), ulcerative colitis (n=5), and pancreatic insufficiency (n=5). In total, 27 (21.4%) patients underwent some form of GI surgery. These surgeries included roux-en-Y gastric bypass (n=4), ileocolonic valve resection (n=5), small or large bowel resection (n=11), pancreatectomy (n=3) or partial or full gastrectomy (n=2). The surgeries were not mutually exclusive.

Of the 126 patients, 66 (52%) tested positive for SIBO, while 60 patients (48%) tested negative for SIBO. Among the 66 who tested positive, 49 were positive for anaerobic bacterial overgrowth and 17 were positive for mixed anaerobic and aerobic overgrowth. None were positive for aerobic bacterial overgrowth alone. All healthy individuals tested negative for SIBO.

Interestingly there was a positive correlation between SIBO and recent antibiotic exposure (odds ratio of 4.2; 95% CI: 1.05 to 24.3; p=0.028, Fisher's exact test). There was no correlation between SIBO and any indication for testing (p=0.19, Fisher's exact test with Monte Carlo simulation, 10,000 replicates), age, gastrointestinal surgery, or PPI use (all p>0.1, Fisher's exact test).

Duodenal Aspirate Microbiome is Altered in Symptomatic Patients

The 16S rRNA-based microbial community composition was determined in duodenal aspirates from the patients with gastrointestinal symptoms (n=126; Table 1) and compared with the microbiome of similarly collected duodenal aspirates from healthy volunteers (n=38; 30% male; age 19-60 years, median 43 years).

TABLE 1

| studyID# | Age | Sex | Race | BMI (kg/m2) | Indication for SB aspirates | Aspirate Micro | Antibiotic treatment (if indicated) | Response | PPI | Abx (</=4 wks before EGD) | history of GI Surgery |
|---|---|---|---|---|---|---|---|---|---|---|---|
| 1 | 53 | 1 | 0 | 35.7 | 0 | 3 | 5 | | 0 | 0 | 0 |
| 2 | 30 | 0 | 0 | 41.15 | 0 | 3 | 5 | | 0 | 0 | 0 |
| 4 | 41 | 1 | 0 | 19.94 | 1 | 0 | 2 | 0 | 2 | 0 | 4 |
| 5 | 78 | 1 | 0 | 24.02 | 0 | 0 | 5 | | 5 | 0 | 2 |
| 6 | 59 | 1 | 0 | 37.02 | 3 | 2 | 5 | | 0 | 0 | 1 |
| 10 | 50 | 1 | 0 | 22.92 | 0 | 0 | 5 | | 2 | 0 | 0 |
| 11 | 81 | 1 | 0 | 21.68 | 0 | 3 | 5 | | 0 | 0 | 0 |
| 12 | 56 | 1 | 0 | 39.48 | 3 | 0 | 4 | 1 | 0 | 0 | 0 |
| 13 | 82 | 1 | 0 | 22.94 | 0 | 3 | 5 | | 4 | 0 | 4 |
| 15 | 47 | 1 | 0 | 22.48 | 0 | 3 | 5 | | 5 | 0 | 4 |
| 16 | 42 | 0 | 4 | 27.9 | 6 | 0 | 5 | | 5 | 0 | 0 |
| 18 | 62 | 1 | 0 | 29.41 | 3 | 3 | 5 | | 0 | 0 | 3 |
| 19 | 18 | 1 | 0 | 27.47 | 3 | 3 | 5 | | 0 | 0 | 4 |
| 21 | 53 | 1 | 0 | 20.91 | 0 | 0 | 5 | | 5 | 0 | 0 |
| 24 | 64 | 1 | 0 | 32.01 | 0 | 0 | 2, 3 | 1 | 5 | 0 | 4 |

TABLE 1-continued

| studyID# | Age | Sex | Race | BMI (kg/m2) | Indication for SB aspirates | Aspirate Micro | Antibiotic treatment (if indicated) | Response | PPI | Abx (</=4 wks before EGD) | history of GI Surgery |
|---|---|---|---|---|---|---|---|---|---|---|---|
| 3 | 49 | 1 | 0 | 34.95 | 3 | 3 | 5 | | 0 | 1 | 0 |
| 17 | 52 | 0 | 0 | 24.4 | 0 | 3 | 5 | | 5 | 0 | 0 |
| 20 | 36 | 1 | 0 | 15.79 | 0 | 3 | 5 | | 5 | 0 | 0 |
| 27 | 34 | 1 | 0 | 33.63 | 0 | 0 | 5 | 1 | 2 | 0 | 0 |
| 28 | 55 | 1 | 0 | 25.32 | 0 | 0 | 5 | | 5 | 0 | 0 |
| 29 | 71 | 0 | 0 | 23.04 | 1 | 2 | 0 | 0 | 0 | 0 | 0 |
| 30 | 82 | 1 | 0 | 20.23 | 0 | 3 | 5 | | 5 | 0 | 0 |
| 32 | 65 | 1 | 0 | 23.14 | 0 | 0 | 2 | 1 | 5 | 1 | 0 |
| 33 | 60 | 1 | 0 | 35.01 | 1 | 0 | 5 | | 2 | 0 | 0 |
| 35 | 15 | 1 | 0 | 22.14 | 1 | 0 | 5 | | 0 | 0 | 0 |
| 36 | 67 | 1 | 0 | 33.6 | 1 | 3 | 5 | | 5 | 0 | 0 |
| 39 | 51 | 1 | 0 | 28.18 | 0 | 3 | 5 | | 0 | 0 | 3 |
| 44 | 83 | 0 | 0 | 35.74 | 2 | 3 | 5 | | 5 | 0 | 0 |
| 68 | 54 | 0 | 0 | 29.34 | 3 | 3 | 5 | | 5 | 0 | 0 |
| 69 | 79 | 0 | 0 | 20.78 | 0 | 0 | 6 | 0 | 5 | 0 | 0 |
| 74 | 35 | 1 | 0 | 33.96 | 0 | 0 | 4 | 1 | 5 | 0 | 1 |
| 75 | 32 | 1 | 0 | 24.2 | 1 | 3 | 5 | | 0 | 0 | 0 |
| 77 | 29 | 1 | 0 | 36.26 | 0 | 3 | 5 | | 5 | 0 | 0 |
| 79 | 57 | 0 | 0 | 16.96 | 4 | 3 | 5 | | | 0 | 0 |
| 81 | 40 | 0 | 0 | 25.78 | 3 | 0 | 5 | | 2 | 0 | 0 |
| 82 | 61 | 0 | 0 | 25.42 | 0 | 0 | 5 | | 0 | 0 | 0 |
| 84 | 50 | 0 | 0 | 24.58 | 2 | 3 | 5 | | 0 | 0 | 0 |
| 87 | 58 | 1 | 0 | 35.44 | 0 | 0 | 5 | | 0 | 0 | 0 |
| 89 | 47 | 1 | 0 | 26.99 | 1 | 0 | 7 | | 1 | 0 | 0 |
| 90 | 64 | 1 | 0 | 18.37 | 6 | 3 | 5 | | 5 | 0 | 0 |
| 94 | 63 | 0 | 0 | 26.56 | 3 | 0 | 5 | | 0 | 0 | 0 |
| 95 | 75 | 1 | 0 | 33.79 | 4 | 3 | 5 | | 0 | 0 | 0 |
| 96 | 64 | 1 | 0 | 41.67 | 3 | 0 | 0 | | | 0 | 0 |
| 97 | 20 | 1 | 0 | 26.96 | 4 | 3 | 5 | | 5 | 0 | 0 |
| 98 | 48 | 0 | 0 | 31.96 | 6 | 3 | 5 | | 5 | 0 | 0 |
| 100 | 53 | 0 | 5 | 32.71 | 0 | 3 | 5 | | 5 | 0 | 0 |
| 108 | 89 | 1 | 0 | 22.77 | 0 | 0 | 0 | 1 | 5 | 0 | 0 |
| 109 | 21 | 1 | 0 | 26.32 | 4 | 3 | 5 | | 5 | 0 | 0 |
| 110 | 30 | 1 | 0 | 22.18 | 0 | 0 | 4 | | 5 | 0 | 0 |
| 112 | 45 | 1 | 0 | 21.63 | 0 | 3 | 5 | | 5 | 0 | 0 |
| 113 | 56 | 1 | 0 | 26.99 | 6 | 0 | 5 | | 2 | 0 | 0 |
| 117 | 56 | 1 | 0 | 31.16 | 0 | 3 | 5 | | 5 | 0 | 0 |
| 121 | 77 | 0 | 0 | 23.85 | 1 | 2 | 0 | 1 | 2 | 0 | 0 |
| 124 | 67 | 1 | 0 | 40.94 | 0 | 0 | 0 | 1 | 2 | 0 | 0 |
| 127 | 27 | 1 | 0 | 38.06 | 0 | 3 | 5 | | 2 | 1 | 0 |
| 128 | 68 | 0 | 0 | 23.22 | 1 | 0 | 4 | | 0 | 0 | 0 |
| 129 | 37 | 1 | 0 | 37.48 | 0 | 3 | 5 | | 5 | 0 | 0 |
| 132 | 62 | 1 | 0 | 29.49 | 1 | 0 | 0 | 1 | 0 | 0 | 2 |
| 134 | 66 | 0 | 0 | 22.34 | 0 | 2 | 2, 4 | | 5 | 1 | 4 |
| 136 | 27 | 1 | 0 | 21.3 | 3 | 0 | 5 | | 5 | 0 | 0 |
| 137 | 36 | 1 | 0 | 39.3 | 3 | 2 | 4 | | 2 | 0 | 3 |
| 138 | 69 | 1 | 0 | 17.26 | 0 | 0 | 4 | 0 | 5 | 0 | 3 |
| 139 | 65 | 1 | 0 | 34.97 | 1 | 0 | 3 | 0 | 2 | 1 | 0 |
| 140 | 57 | 1 | 0 | 19.3 | 1 | 2 | 0 | 1 | 5 | 1 | 0 |
| 142 | 21 | 1 | 0 | 25.13 | 0 | 3 | 5 | | 5 | 0 | 0 |
| 147 | 81 | 1 | 0 | 21.24 | 0 | 0 | 4 | 1 | 5 | 0 | 0 |
| 148 | 45 | 1 | 1 | 27.92 | 3 | 3 | 5 | | 5 | 0 | 0 |
| 150 | 17 | 1 | 0 | 21.98 | 3 | 3 | 5 | | 5 | 0 | 0 |
| 152 | 51 | 1 | 0 | 22.09 | 3 | 0 | 5 | | 4 | 0 | 0 |
| 153 | 60 | 1 | 0 | 24.61 | 0 | 3 | 5 | | 5 | 0 | 3 |
| 154 | 52 | 1 | 0 | 39 | 0 | 3 | 5 | | 5 | 0 | 2 |
| 160 | 68 | 1 | 0 | 19.06 | 3 | 3 | 5 | | 5 | 0 | 0 |
| 166 | 32 | 1 | 0 | 33.5 | 1 | 3 | 5 | | 0 | 0 | 0 |
| 168 | 37 | 1 | 0 | 33.79 | 0 | 3 | 5 | | 5 | 0 | 0 |
| 170 | 35 | 1 | 0 | 24.05 | 6 | 3 | 5 | | 4 | 0 | 0 |
| 171 | 22 | 1 | 0 | 23.35 | 0 | 3 | 5 | | 5 | 0 | 0 |
| 173 | 59 | 1 | 0 | 19.98 | 3 | 0 | 4 | 0 | 0 | 1 | 3 |
| 177 | 68 | 1 | 0 | 24.08 | 3 | 2 | 8 | | 1 | 0 | 0 |
| 179 | 62 | 1 | 0 | 19.46 | 0 | 2 | 4 | | 2 | 1 | 1 |
| 183 | 70 | 1 | 0 | 19.76 | 3 | 0 | 4 | 1 | 5 | 0 | 0 |
| 184 | 61 | 1 | 0 | 22.42 | 3 | 3 | 5 | | 5 | 0 | 0 |
| 185 | 34 | 1 | 0 | 19.94 | 0 | 0 | 5 | | 5 | 0 | 0 |
| 186 | 62 | 1 | 0 | 31.48 | 1 | 2 | 0 | | 1 | 0 | 4 |
| 187 | 63 | 1 | 0 | 31.24 | 4 | 0 | 0 | 1 | 2 | 0 | 2, 3 |
| 188 | 75 | 1 | 0 | 20.78 | 3 | 2 | 4 | 1 | 5 | 0 | 3 |
| 189 | 67 | 1 | 0 | 31.22 | 0 | 3 | 5 | | 5 | 0 | 3 |
| 191 | 59 | 1 | 0 | 24.42 | 2 | 3 | 5 | | 5 | 0 | 0 |
| 192 | 66 | 1 | 0 | 24.34 | 6 | 0 | 5 | | | 0 | 0 |
| 193 | 35 | 1 | 4 | 21.23 | 4 | 3 | 5 | | 5 | 0 | 2, 3 |
| 194 | 74 | 0 | 0 | 22.5 | 1 | 2 | 9 | | 2 | 1 | 0 |

TABLE 1-continued

| studyID# | Age | Sex | Race | BMI (kg/m2) | Indication for SB aspirates | Aspirate Micro | Antibiotic treatment (if indicated) | Response | PPI | Abx (</=4 wks before EGD) | history of GI Surgery |
|---|---|---|---|---|---|---|---|---|---|---|---|
| 195 | 53 | 1 | 0 | 21.34 | 0 | 0 | 4 | 0 | 5 | 0 | mets endometrial CA w/carcinomatosis & sigmoid stricture |
| 196 | 64 | 1 | 0 | 29.3 | 4 | 2 | 0 | 0 | 5 | 1 | 1, 2 |
| 199 | 60 | 0 | 0 | 33.1 | 0 | 3 | 5 | | 5 | 0 | 0 |
| 200 | 31 | 0 | 0 | 21 | 0 | 3 | 5 | | 5 | 0 | 0 |
| 201 | 54 | 1 | 0 | 23.6 | 3 | 3 | 5 | | 5 | 0 | UC s/p colectomy w/IPAA & extensive adhesions |
| 203 | 38 | 1 | 0 | 23.01 | 0 | 0 | 5 | | 5 | 0 | 0 |
| 204 | 23 | 1 | 0 | 24.28 | 1 | 0 | 5 | | 5 | 0 | 0 |
| 205 | 18 | 1 | 0 | 22.6 | 3 | 0 | 4 | | 5 | 0 | 0 |
| 206 | 77 | 0 | 0 | 28 | 2 | 3 | 5 | | 0 | 0 | 0 |
| 207 | 24 | 1 | 0 | 43.72 | 3 | 0 | 5 | | 5 | 0 | 0 |
| 211 | 71 | 1 | 0 | 28 | 0 | 3 | 5 | | 5 | 0 | 0 |
| 212 | 73 | 0 | 0 | 22.3 | 3 | 0 | 5 | | 5 | 0 | 4 |
| 213 | 28 | 0 | 0 | 22.8 | 3 | 3 | 5 | | 2 | 0 | 4 |
| 214 | 58 | 1 | 0 | 32.1 | 3 | 0 | 8 | | 1 | 0 | 0 |
| 216 | 26 | 1 | 0 | 26.67 | 3 | 3 | 5 | | 0 | 0 | 0 |
| 217 | 59 | 0 | 0 | 30.72 | 0 | 3 | 5 | | 5 | 0 | 0 |
| 218 | 58 | 1 | 0 | 27.63 | 0 | 3 | 5 | | 0 | 0 | 0 |
| 219 | 69 | 1 | 0 | 29.98 | 0 | 3 | 5 | | 0 | 0 | 1 |
| 220 | 83 | 1 | 0 | 18.96 | 0 | 3 | 5 | | 5 | 0 | 4 |
| 221 | 56 | 1 | 0 | 30.04 | 0 | 3 | 5 | | 1 | 0 | 0 |
| 222 | 60 | 0 | 0 | 27.78 | 0 | 3 | 5 | | 5 | 0 | 0 |
| 224 | 28 | 1 | 0 | 27.51 | 0 | 3 | 5 | | 5 | 0 | 0 |
| 226 | 72 | 1 | 0 | 18.26 | 0 | 3 | 5 | | 5 | 0 | 0 |
| 227 | 50 | 1 | 0 | 22.29 | 3 | 3 | 5 | | 5 | 0 | 0 |
| 228 | 76 | 0 | 0 | 33.18 | 3 | 2 | 5 | | 0 | 0 | 0 |
| 229 | 75 | 1 | 0 | 27.94 | 0 | 2 | 4 | | 5 | 0 | 0 |
| 231 | 29 | 1 | 0 | 18.68 | 4 | 3 | 5 | | 5 | 0 | 0 |
| 232 | 56 | 1 | 4 | 30.29 | 3 | 2 | 5 | | 0 | 0 | 0 |
| 233 | 39 | 1 | 0 | 43.77 | 0 | 0 | 0 | 1 | 2 | 0 | 0 |
| 234 | 31 | 1 | 0 | 22.04 | 3 | 0 | 5 | | 0 | 0 | 0 |
| 235 | 52 | 1 | 0 | 30.71 | 0 | 0 | 5 | | 0 | 0 | 0 |
| 237 | 45 | 1 | 0 | 20.85 | 3 | 3 | 5 | | 5 | 0 | 0 |
| 239 | 67 | 1 | 0 | 31.52 | 3 | 3 | 5 | | 5 | 0 | 0 |
| 241 | 62 | 0 | 0 | 26.87 | 0 | 2 | 5 | | 5 | 1 | 0 |
| 242 | 35 | 1 | 0 | 24.63 | 4 | 3 | 5 | | 5 | 0 | 0 |
| 246 | 60 | 1 | 0 | 34.01 | 0 | 0 | 5 | | 1 | 0 | 0 |
| 251 | 32 | 1 | 0 | 31.14 | 3 | 3 | 5 | | 0 | 0 | 0 |
| 254 | 28 | 1 | 0 | 20.53 | 3 | 3 | 5 | | 5 | 0 | 0 |
| 255 | 45 | 0 | 0 | 25.05 | 2 | 0 | 4 | | 5 | 0 | 0 |
| 259 | 64 | 0 | 0 | 31.39 | 1 | 2 | 5 | | 2 | 0 | 4 |
| 261 | 65 | 1 | 0 | 28.27 | 3 | 3 | 5 | | 5 | 0 | 0 |
| 265 | 43 | 1 | 0 | 25.1 | 3 | 0 | 5 | | 5 | 1 | 0 |
| 268 | 66 | 0 | 0 | 31.27 | 1 | 3 | 5 | | 0 | 0 | 0 |
| 269 | 23 | 1 | 0 | 21.4 | 3 | 3 | 5 | | 5 | 0 | 0 |
| 272 | 50 | 1 | 0 | 25.22 | 0 | 3 | 5 | | 5 | 0 | 0 |
| 274 | 26 | 1 | 0 | 19.45 | 3 | 3 | 5 | | 0 | 0 | 0 |
| 275 | 32 | 1 | 0 | 47.51 | 3 | 0 | 5 | | 5 | 0 | 1 |
| 276 | 33 | 1 | 0 | 31.52 | 0 | 0 | 4 | | 5 | 1 | 0 |
| 279 | 32 | 1 | 0 | 45.69 | 1 | 3 | 5 | | 1 | 0 | 0 |
| 280 | 36 | 1 | 0 | 20.95 | 0 | 3 | 5 | | 2 | 1 | 3 |
| 281 | 69 | 1 | 0 | 26.33 | 0 | 3 | 5 | | 5 | 0 | 0 |
| 284 | 37 | 0 | 0 | 26.78 | 0 | 3 | 5 | | 5 | 0 | 0 |
| 285 | 46 | 1 | 0 | 25.5 | 0 | 0 | 5 | | 5 | 1 | 0 |
| 400 | 46 | 1 | | | | 7 | 3 | | | | |
| 401 | 35 | 1 | | | | 7 | 3 | | | | |
| 402 | 31 | 1 | | | | 7 | 3 | | | | |
| 403 | 48 | 1 | | | | 7 | 3 | | | | |
| 404 | 50 | 1 | | | | 7 | 3 | | | | |
| 405 | 43 | 1 | | | | 7 | 3 | | | | |
| 406 | 41 | 1 | | | | 7 | 3 | | | | |
| 407 | 23 | 1 | | | | 7 | 3 | | | | |
| 408 | 51 | 0 | | | | 7 | 3 | | | | |
| 409 | 36 | 0 | | | | 7 | 3 | | | | |
| 410 | 40 | 0 | | | | 7 | 3 | | | | |
| 411 | 58 | 0 | | | | 7 | 3 | | | | |
| 412 | 49 | 1 | | | | 7 | 3 | | | | |
| 413 | 26 | 1 | | | | 7 | 3 | | | | |
| 414 | 44 | 0 | | | | 7 | 3 | | | | |
| 415 | 30 | 0 | | | | 7 | 3 | | | | |
| 416 | 53 | 0 | | | | 7 | 3 | | | | |
| 417 | 25 | 0 | | | | 7 | 3 | | | | |
| 418 | 21 | 0 | | | | 7 | 3 | | | | |

TABLE 1-continued

| studyID# | Age | Sex | Race | BMI (kg/m2) | Indication for SB aspirates | Aspirate Micro | Antibiotic treatment (if indicated) | Response | PPI | Abx (</=4 wks before EGD) | history of GI Surgery |
|---|---|---|---|---|---|---|---|---|---|---|---|
| 419 | 55 | 0 | | | 7 | 3 | | | | | |
| 420 | 36 | 1 | | | 7 | 3 | | | | | |
| 421 | NA | NA | | | 7 | 3 | | | | | |
| 422 | 45 | 1 | | | 7 | 3 | | | | | |
| 423 | 48 | 1 | | | 7 | 3 | | | | | |
| 424 | 34 | 1 | | | 7 | 3 | | | | | |
| 425 | 59 | 1 | | | 7 | 3 | | | | | |
| 426 | 28 | 1 | | | 7 | 3 | | | | | |
| 427 | 43 | 1 | | | 7 | 3 | | | | | |
| 428 | 51 | 1 | | | 7 | 3 | | | | | |
| 429 | 23 | 1 | | | 7 | 3 | | | | | |
| 430 | 43 | 1 | | | 7 | 3 | | | | | |
| 431 | 52 | 1 | | | 7 | 3 | | | | | |
| 432 | 56 | 1 | | | 7 | 3 | | | | | |
| 433 | 52 | 1 | | | 7 | 3 | | | | | |
| 434 | 46 | 1 | | | 7 | 3 | | | | | |
| 435 | 19 | 1 | | | 7 | 3 | | | | | |
| 436 | 36 | 0 | | | 7 | 3 | | | | | |
| 437 | 60 | 1 | | | 7 | 3 | | | | | |
| 438 | | | | | 7 | 3 | | | | | |

Sex: 0 = M, 1 = F
Race: 0 = white, 1 = black, 2 = hispanic, 3 = asian, 4 = other, 5 = N/A
Indication for SB aspirates: 0 = diarrhea, 1 = bloating, 2 = weight loss, 3 = abd pain, 4 = N/V, 5 = nutr deficiency, 6 = none/unclear, 7 = healthy
Aspirate Micro (>100,000 cfu/mL): 0 = anaerobic, 1 = aerobic, 2 = both, 3 = negative
Antibiotic treatment: 0 = cipro, 1 = amoxicillin/clavulanate, 2 = TMP-SMX, 3 = metronidazole, 4 = rifaximin, 5 = none, 6 = amoxicillin, 7 = neomycin, 8 = doxycycline, 9 = vanc
Response: 0 = N, 1 = Y
PPI: 0 = omep, 1 = esomep, 2 = pantop, 3 = rabep, 4= lansop, 5 = none
Abx </= 4 wks before EGD: 0 = N, 1 = Y
history of GI Surgery: 0 = none, 1 = RYGB, 2 = IC valve resection, 3 = bowel resection, 4 = other Significant differences were observed in phylogenetic unweighted UniFrac-based ($p<0.001$, PERMANOVA; FIG. 1A) and non-phylogenetic Bray Curtis-based ($p<0.001$, PERMANOVA; FIG. 1B) beta diversity between small intestinal microbial communities from symptomatic patients and healthy volunteers. There were significant differences in relative abundance at multiple taxonomic levels ($q<0.05$, permutation test with t-statistic; FIG. 2, Table 2) when comparing the two communities, which included significant decreases in *Porphyromonas*, *Prevotella*, and *Fusobacterium* in symptomatic patients. The small intestinal microbial communities from symptomatic patients were characterized by significantly lower phylogenetic alpha diversity, richness, and evenness ($p<0.0001$ for each, t-test; FIG. 1C-E).

TABLE 2

| | P-value* | Q-value** | Mean abundance in healthy | Mean abundance in symptomatic | log2 (Fold Change) |
|---|---|---|---|---|---|
| Phylum | | | | | |
| Actinobacteria | 0.001 | 0.001 | 0.0569 | 0.1091 | 0.94 |
| Bacteroidetes | 0.001 | 0.001 | 0.1248 | 0.0346 | −1.85 |
| Fusobacteria | 0.001 | 0.001 | 0.0436 | 0.0241 | −0.86 |
| Spirochaetes | 0.001 | 0.001 | 0.0011 | 0.0001 | −3.03 |
| Synergistetes | 0.001 | 0.001 | 0.0004 | 0.0001 | −2.13 |
| Tenericutes | 0.001 | 0.001 | 0.0006 | 0.0001 | −3.43 |
| Class | | | | | |
| Actinobacteria; Actinobacteria | 0.002 | 0.004 | 0.0543 | 0.1017 | 0.91 |
| Actinobacteria; Coriobacteriia | 0.005 | 0.009 | 0.0026 | 0.0074 | 1.53 |
| Bacteroidetes; Bacteroidia | 0.001 | 0.002 | 0.1206 | 0.0332 | −1.86 |
| Bacteroidetes; Flavobacteriia | 0.001 | 0.002 | 0.0042 | 0.0014 | −1.60 |
| Fusobacteria; Fusobacteriia | 0.001 | 0.002 | 0.0436 | 0.0241 | −0.86 |
| Proteobacteria; Betaproteobacteria | 0.001 | 0.002 | 0.0498 | 0.0142 | −1.81 |
| Proteobacteria; Epsilonproteobacteria | 0.001 | 0.002 | 0.0051 | 0.0017 | −1.59 |
| Spirochaetes; Spirochaetia | 0.001 | 0.002 | 0.0011 | 0.0001 | −3.03 |
| Synergistetes; Synergistia | 0.001 | 0.002 | 0.0004 | 0.0001 | −2.13 |
| Tenericutes; Mollicutes | 0.001 | 0.002 | 0.0006 | 0.0001 | −3.43 |
| Order | | | | | |
| Actinobacteria; Bifidobacteriales | 0.019 | 0.039 | 0.0003 | 0.0048 | 4.01 |
| Actinobacteria; Coriobacteriales | 0.006 | 0.015 | 0.0025 | 0.0072 | 1.51 |
| Bacteroidetes; Bacteroidales | 0.001 | 0.003 | 0.1206 | 0.0332 | −1.86 |
| Bacteroidetes; Flavobacteriales | 0.001 | 0.003 | 0.0042 | 0.0014 | −1.60 |
| Firmicutes; Selenomonadales | 0.002 | 0.005 | 0.0033 | 0.0016 | −1.06 |
| Fusobacteria; Fusobacteriales | 0.001 | 0.003 | 0.0436 | 0.0241 | −0.86 |
| Proteobacteria; Campylobacterales | 0.001 | 0.003 | 0.0051 | 0.0017 | −1.59 |

TABLE 2-continued

|  | P-value* | Q-value** | Mean abundance in healthy | Mean abundance in symptomatic | log2 (Fold Change) |
|---|---|---|---|---|---|
| Proteobacteria; Cardiobacteriales | 0.008 | 0.018 | 0.0002 | 0.0001 | −1.93 |
| Proteobacteria; Neisseriales | 0.001 | 0.003 | 0.0484 | 0.0125 | −1.95 |
| Proteobacteria; Pasteurellales | 0.001 | 0.003 | 0.0705 | 0.0272 | −1.37 |
| Spirochaetes; Spirochaetales | 0.001 | 0.003 | 0.0011 | 0.0001 | −3.03 |
| Synergistetes; Synergistales | 0.001 | 0.003 | 0.0004 | 0.0001 | −2.13 |
| Tenericutes; Mycoplasmatales | 0.001 | 0.003 | 0.0006 | 0.0001 | −3.43 |
| Family | | | | | |
| Actinobacteria; Atopobiaceae | 0.006 | 0.018 | 0.0025 | 0.0072 | 1.51 |
| Actinobacteria; Bifidobacteriaceae | 0.019 | 0.043 | 0.0003 | 0.0048 | 4.01 |
| Bacteroidetes; Flavobacteriaceae | 0.001 | 0.004 | 0.0042 | 0.0014 | −1.60 |
| Bacteroidetes; Porphyromonadaceae | 0.001 | 0.004 | 0.0199 | 0.0046 | −2.11 |
| Bacteroidetes; Prevotellaceae | 0.001 | 0.004 | 0.1000 | 0.0284 | −1.82 |
| Bacteroidetes; Tannerellaceae | 0.001 | 0.004 | 0.0007 | 0.0002 | −2.07 |
| Firmicutes; Peptostreptococcaceae | 0.004 | 0.013 | 0.0092 | 0.0064 | −0.53 |
| Firmicutes; Selenomonadaceae | 0.002 | 0.007 | 0.0033 | 0.0016 | −1.06 |
| Fusobacteria; Fusobacteriaceae | 0.001 | 0.004 | 0.0318 | 0.0144 | −1.14 |
| Fusobacteria; Leptotrichiaceae | 0.012 | 0.029 | 0.0119 | 0.0097 | −0.30 |
| Proteobacteria; Campylobacteraceae | 0.001 | 0.004 | 0.0051 | 0.0017 | −1.59 |
| Proteobacteria; Cardiobacteriaceae | 0.008 | 0.022 | 0.0002 | 0.0001 | −1.93 |
| Proteobacteria; Neisseriaceae | 0.001 | 0.004 | 0.0484 | 0.0125 | −1.95 |
| Proteobacteria; Pasteurellaceae | 0.001 | 0.004 | 0.0705 | 0.0272 | −1.37 |
| Spirochaetes; Spirochaetaceae | 0.001 | 0.004 | 0.0011 | 0.0001 | −3.03 |
| Synergistetes; Synergistaceae | 0.001 | 0.004 | 0.0004 | 0.0001 | −2.13 |
| Tenericutes; Mycoplasmataceae | 0.001 | 0.004 | 0.0006 | 0.0001 | −3.43 |
| Unclassified_Family | 0.011 | 0.028 | 0.0535 | 0.0383 | −0.48 |
| Genus | | | | | |
| Actinobacteria; *Atopobium* | 0.008 | 0.024 | 0.0025 | 0.0069 | 1.48 |
| Actinobacteria; *Scardovia* | 0.013 | 0.035 | 0.0000 | 0.0008 | 4.92 |
| Bacteroidetes; *Alloprevotella* | 0.001 | 0.004 | 0.0106 | 0.0004 | −4.73 |
| Bacteroidetes; *Capnocytophaga* | 0.001 | 0.004 | 0.0030 | 0.0010 | −1.57 |
| Bacteroidetes; *Chryseobacterium* | 0.001 | 0.004 | 0.0012 | 0.0004 | −1.66 |
| Bacteroidetes; *Porphyromonas* | 0.001 | 0.004 | 0.0199 | 0.0046 | −2.11 |
| Bacteroidetes; *Prevotella* | 0.001 | 0.004 | 0.0894 | 0.0280 | −1.67 |
| Bacteroidetes; *Tannerella* | 0.001 | 0.004 | 0.0007 | 0.0002 | −2.07 |
| Firmicutes; *Butyrivibrio* | 0.001 | 0.004 | 0.0005 | 0.0001 | −2.24 |
| Firmicutes; *Catonella* | 0.007 | 0.023 | 0.0019 | 0.0012 | −0.75 |
| Firmicutes; *Filifactor* | 0.001 | 0.004 | 0.0019 | 0.0002 | −3.50 |
| Firmicutes; *Gemella* | 0.011 | 0.031 | 0.0535 | 0.0383 | −0.48 |
| Firmicutes; *Mogibacterium* | 0.015 | 0.039 | 0.0011 | 0.0028 | 1.29 |
| Firmicutes; *Moryella* | 0.001 | 0.004 | 0.0022 | 0.0010 | −1.14 |
| Firmicutes; *Selenomonas* | 0.002 | 0.007 | 0.0033 | 0.0016 | −1.06 |
| Fusobacteria; *Fusobacterium* | 0.001 | 0.004 | 0.0318 | 0.0144 | −1.14 |
| Fusobacteria; *Leptotrichia* | 0.02 | 0.050 | 0.0108 | 0.0094 | −0.20 |
| Fusobacteria; *Streptobacillus* | 0.001 | 0.004 | 0.0011 | 0.0003 | −2.03 |
| Proteobacteria; *Campylobacter* | 0.001 | 0.004 | 0.0051 | 0.0017 | −1.59 |
| Proteobacteria; *Cardiobacterium* | 0.008 | 0.024 | 0.0002 | 0.0001 | −1.93 |
| Proteobacteria; *Haemophilus* | 0.001 | 0.004 | 0.0703 | 0.0270 | −1.38 |
| Proteobacteria; *Morococcus* | 0.001 | 0.004 | 0.0040 | 0.0011 | −1.88 |
| Proteobacteria; *Neisseria* | 0.001 | 0.004 | 0.0442 | 0.0112 | −1.98 |
| Spirochaetes; *Treponema* | 0.001 | 0.004 | 0.0011 | 0.0001 | −3.03 |
| Synergistetes; *Fretibacterium* | 0.001 | 0.004 | 0.0004 | 0.0001 | −2.13 |
| Tenericutes; *Mycoplasma* | 0.001 | 0.004 | 0.0006 | 0.0001 | −3.43 |

*Permutation test (t-statistic as the test statistic with square-root transformed relative abundances, 1,000 permutations) was used for differential abundance testing. Taxa with prevalence <10% or the maximum proportion <0.2% were excluded from testing.
**False discovery rate control (BH procedure) was performed on each taxonomic level.

Next, the primary microbial determinants responsible for the difference in small intestinal microbiome in symptomatic patients were identified. Random Forest classification was used on the OTU level abundances to develop a symptom index (SI) model for microbial differences associated with symptomatic patients. The resulting index is the out-of-bag (OOB) predicted probability of symptomatic patient group membership; i.e. on a scale of 0 to 1, scores approaching 1 indicate high probability of a microbial community associated with gastrointestinal symptoms. The SI differentiates symptomatic patients from healthy individuals (FIG. 3A), supported by Receiver Operating Characteristic (ROC) curve analysis (area under the curve=0.896, p<0.0001; 95% C.I.: 0.844-0.949, DeLong). Boruta selection yields 26 OTUs that significantly contribute to the classification (FIG. 3B). To determine if patient characteristics contribute to changes in microbiome the clinical metadata obtained from patient medical health records were examined. Advanced age, antibiotic use, history of gastrointestinal surgery, and proton-pump inhibitor use were found to be significantly associated with the SI (FDR q<0.1, linear regression) and these four clinical factors together explain approximately 12.7% of variance ($R^2$) in the SI across all samples (FIG. 3C-F), while sex, BMI, and MO were not significantly associated with SI.

A Subset of Symptomatic Patients have Small Intestinal Microbial Dysbiosis

Notable heterogeneity was found in the small intestinal microbiome of symptomatic patients and a subset of patients appear compositionally distinct from healthy individuals in beta diversity plots (FIG. 1A, B). To further explore this observation samples from symptomatic patients were re-classified as being healthy-like or dysbiotic based on their Aitchison distance to healthy small intestinal microbial communities using the CLOUD neighborhood method. This classification scheme identified 37/38 (97%) healthy volunteers as "healthy-like", while 89 (71%) symptomatic patient communities were found to be healthy-like and 37 (29%) were found to be dysbiotic (based on distance from healthy, FIG. 4A). These groupings were comparable to those achieved by spectral clustering (Table 3). The log-transformed CLOUD statistic for each sample defines the sample's "dysbiosis index" (DI) score (FIG. 4B). Boruta feature selection identified 23 genus-level taxa that contribute significantly to the DI, mostly by their relative absence from dysbiotic communities (FIG. 4C). A significantly higher DI score was found in patients >50 years old and those with history of antibiotic use, proton-pump inhibitor (PPI) use, or gastrointestinal surgery (p<0.05, t-test; FIG. 5A-D), consistent with factors that contributed to the SI. Additionally, there was a significant negative correlation between DI score and phylogenetic diversity, richness, and evenness (p<0.0001, Pearson correlation; FIG. 4D-F).

TABLE 3

Contingency table showing similar dysbiosis classifications using the CLOUD method compared to spectral clustering.

| | | CLOUD | |
| --- | --- | --- | --- |
| | | dysbiotic | healthy-like |
| spectral clustering | cluster 1 | 9 | 119 |
| | cluster 2 | 29 | 7 |

SIBO does not Correlate with Small Intestinal Microbial Dysbiosis

Figure 6:
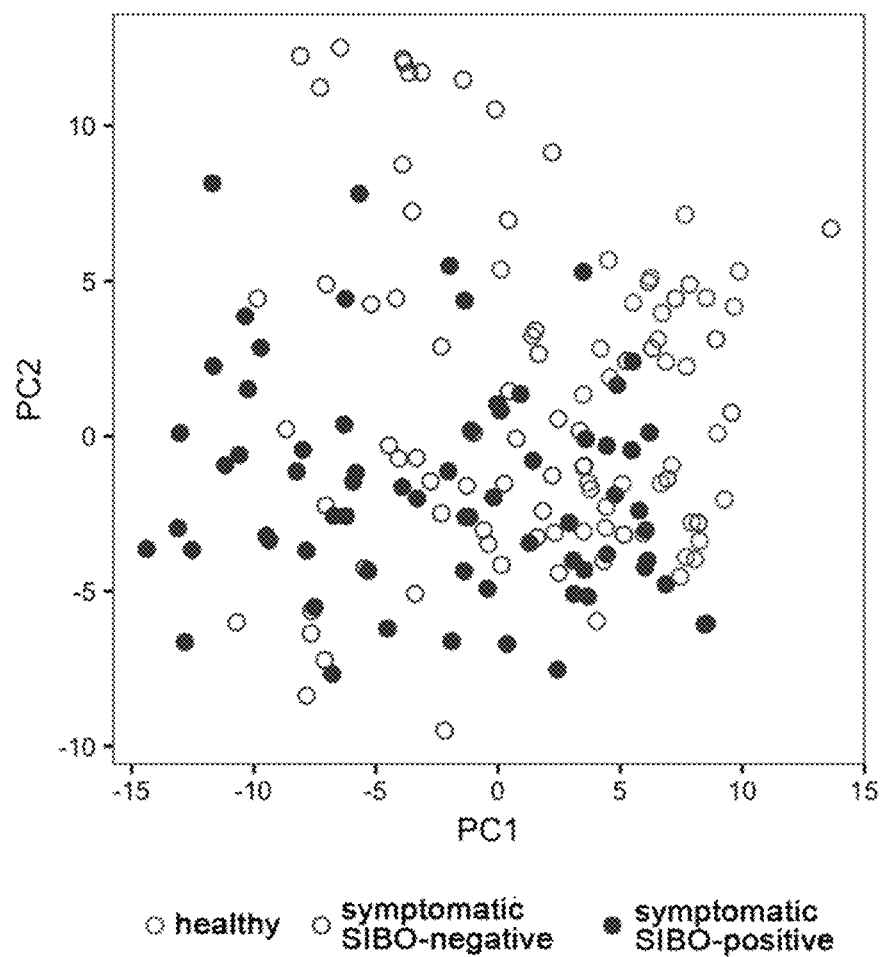
FIG. 6 contains data showing that quantitative small bowel culture does not reflect small bowel microbiome. Distribution of microbial communities from symptomatic patients (blue) with and without SIBO based on Aitchison distance from healthy microbial communities (red). SIBO does not correlate with microbial community as summarized by dysbiosis classification (p=0.33, Fisher's exact test). Open circles represent small bowel microbiomes from individuals who tested negative for SIBO; closed circles represent those tested positive for SIBO by aspirate culture.
Figure 7A:
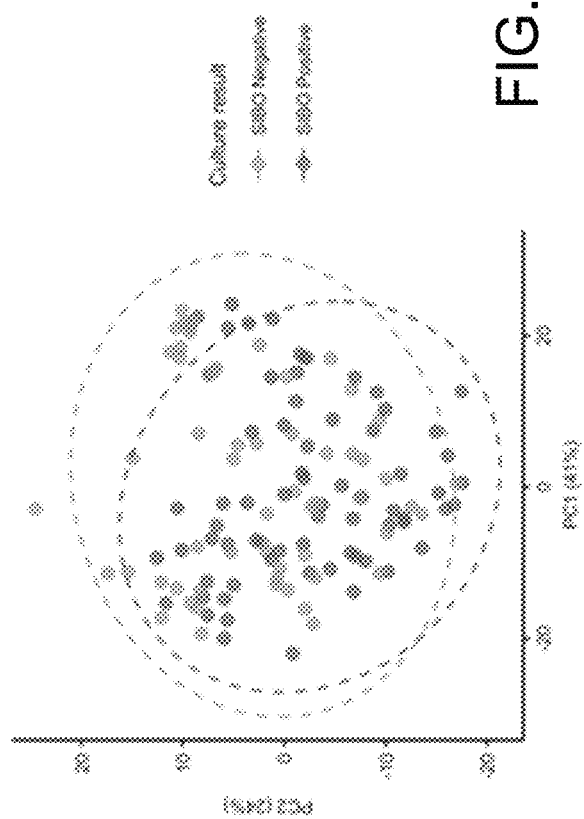
FIGS. 7A-7D contain data showing that microbial diversity is not significantly different among patients with and without SIBO.
Figure 7B:
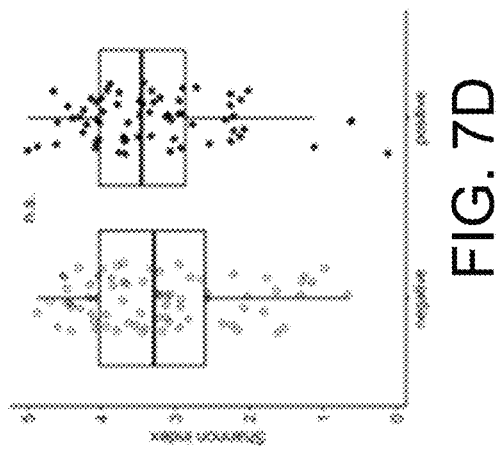
Figure 7C:
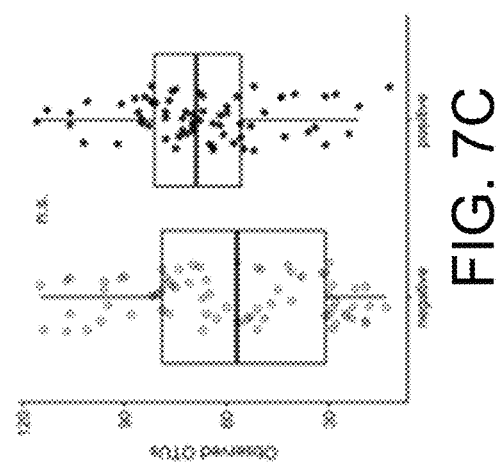
Figure 7D:
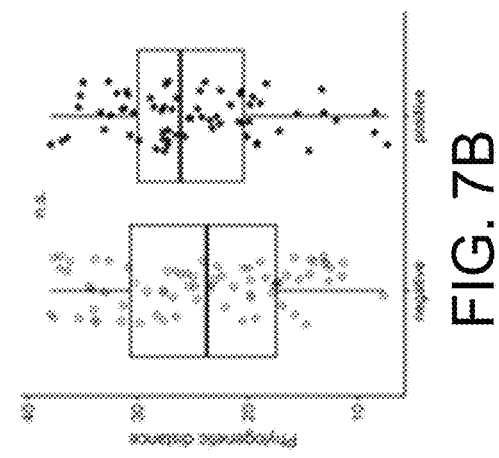

The microbiome of symptomatic patients with and without SIBO were compared and it was found that SIBO does not correlate with small intestinal dysbiosis (p=0.33, Fisher's exact test of culture result vs. dysbiosis classification; FIG. 6). This suggests that some symptomatic patients diagnosed with SIBO in fact have an overabundance of bacteria normally found in healthy microbial communities, while others who do not have SIBO based on quantitative assessment have dysbiosis as defined here. There are no significant differences in alpha or beta diversity among symptomatic patients with and without reported SIBO (FIG. 7A-D).

Imputed Microbial Functional Pathways Suggest Differences in Diet

Figure 8A:
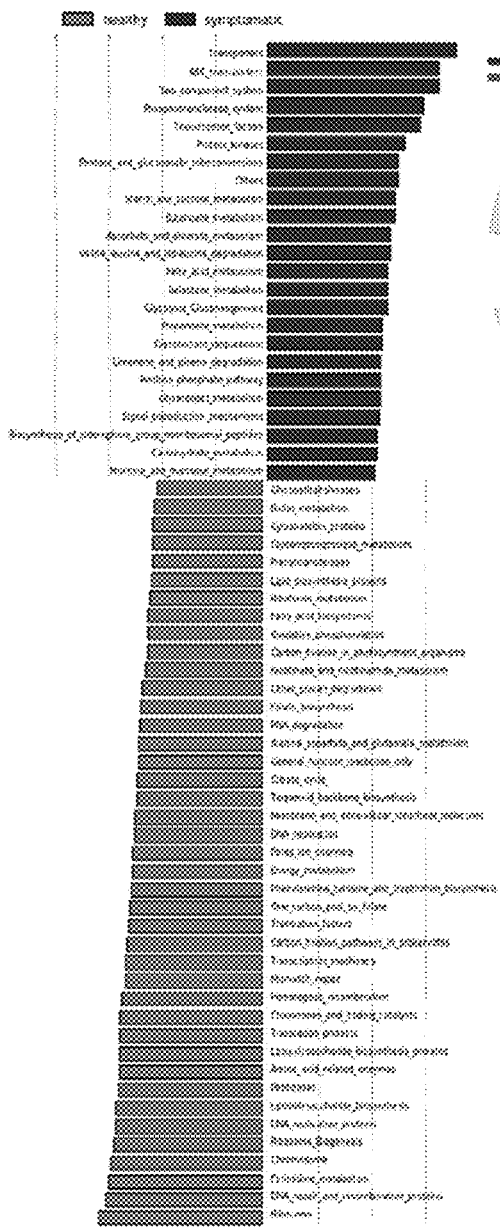
FIGS. 8A-8B contain data showing that complex carbohydrate degradation pathways are enriched in healthy individuals. Differentially abundant microbial functions (LEfSe, LDA>2) at the gene function level (L3.
Figure 8B:
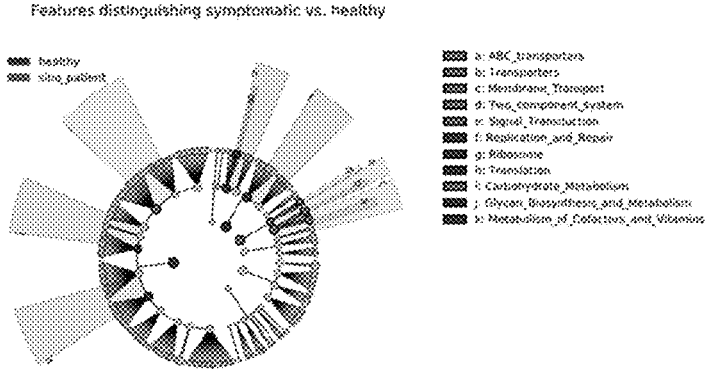

To determine the functional changes associated with differences in microbiome, gut microbial function was imputed from the 16S rRNA-based microbiome using PICRUSt and pathway analysis. Differential predicted genes/pathways were determined using LEfSe (FIG. 8A, B). Pathways reflective of oxidative stress such as ascorbate and aldarate metabolism and biosynthesis of siderophores were enriched in symptomatic patients, consistent with previous reports in dysbiosis. Interestingly, pathways associated with simple sugar metabolism were enriched in symptomatic patients while complex carbohydrate degradation pathways were more prevalent in healthy individuals. Patients' dietary histories were not available as these samples were obtained directly from the clinical microbiology laboratory but the increased prevalence of Prevotella and the enrichment of complex carbohydrate degradation pathways are suggestive of a higher fiber intake in healthy individuals while simple sugar metabolism pathways found in symptomatic patients may reflect a higher dietary intake of simple sugars. These data alone do not provide sufficient evidence to support the role of diet-related changes in small intestinal microbiome in causing gastrointestinal symptoms, but do support this hypothesis. To better address this, a pilot dietary intervention study was performed.

A Subset of Healthy Individuals Eating High Fiber Diets have SIBO

Figures 9A, 9B:
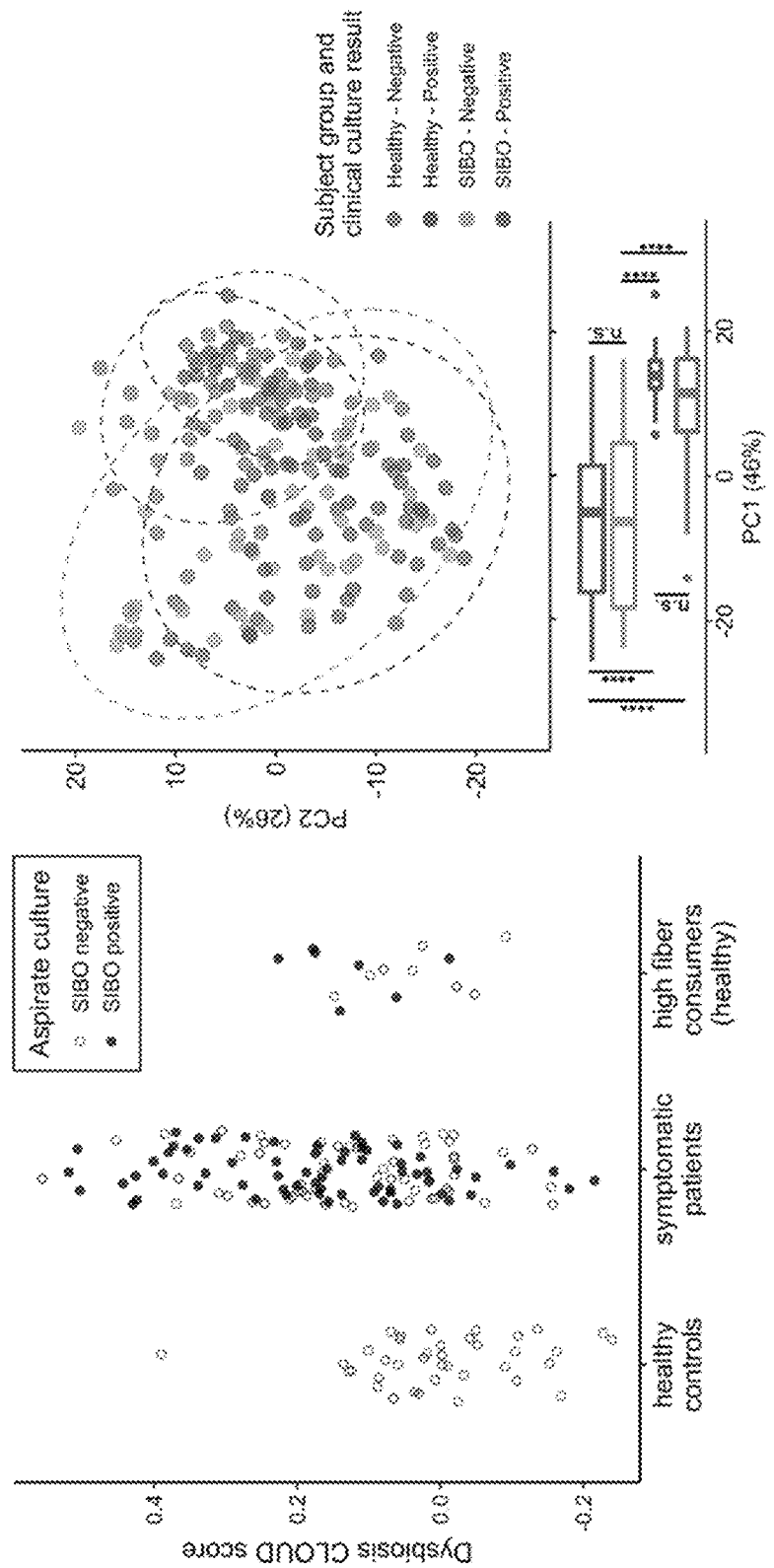
FIGS. 9A-9B contain data showing that a subset of healthy individuals consuming high fiber diet have SIBO. (A) DI and (B) distribution based on Aitchison distance of healthy controls without SIBO (green), symptomatic patients with (red) and without (orange) SIBO, and healthy individuals consuming a high fiber diet with (blue) and without (green) SIBO. ****, q<0.0001; n.s., q>0.05; pair-wise t-test with FDR correction.

As gastrointestinal symptoms were associated with decreased prevalence of Prevotella and potentially increased consumption of simple sugars, it was next tested if a dietary change from high fiber diet to a high simple sugar diet can trigger symptoms in a microbiota-dependent manner. Healthy individuals consuming baseline high fiber diets (>11 g/1000 cal; Table 4) were identified and duodenal aspirates were obtained for quantitative culture and small intestinal microbial community profiling using 16S rRNA gene sequencing. Despite being asymptomatic, 8/16 (50%) subjects on a baseline high fiber diet tested positive for SIBO by the standard culture criteria described above. Microbial community profiles were obtained from only 15 of the 16 participants after quality control and filtering of sequencing data. All subjects had a microbial microbiome representative of a "healthy-like" community (FIG. 9A). The small bowel microbial communities of these high fiber-consuming healthy individuals clustered with the healthy individuals previously tested (FIG. 9B) based on the Aitchison beta diversity for each sample regardless of presence or absence of SIBO. The symptomatic patient microbiomes show wider distribution as noted previously. Accompanying box plots show the distribution of principal coordinate 1, which accounts for 46% of the variance in data, further supporting the conclusion that duodenal microbiome significantly distinguishes healthy and symptomatic individuals (q<0.0001, pairwise t-test with FDR correction; FIG. 9B), but does not distinguish presence or absence of SIBO among healthy or symptomatic individuals (q>0.25, pairwise t-test with FDR correction; FIG. 9B). This suggests that healthy individuals can have SIBO without any symptoms or alterations in microbiome. There are no significant differences in small intestinal microbial alpha or beta diversity or microbial taxa among the healthy subjects with and without SIBO. Therefore, SIBO as currently defined may also result from dietary preferences, such as high fiber consumption, as shown here.

TABLE 4

| | Participants (n = 16) |
| --- | --- |
| Mean age (years) | 26 |
| Sex (female %) | 53.3 |
| Race (Caucasian %) | 73 |
| Mean BMI (kg/m$^2$) | 23.7 |
| Duodenal bacterial growth >100,000 CFU/mL (positive %) | 46.7 |

Short-Term Diet Change Alters Microbial Diversity and Triggers GI Symptoms

It was then addressed whether diet related changes in small intestinal microbiome and function might be responsible, in part, for alterations in epithelial barrier function, and symptoms often associated with FGIDs. To investigate this, a short-term dietary intervention study was performed limiting the consumption of fiber in the 16 healthy individuals consuming baseline high fiber diet (>11 g/1000 cal) identified above. All subjects were placed on a low fiber (<10 g/day), high simple sugar (accounting for >50% daily carbohydrate) diet for 7 days under the direction of a dietitian (FIG. 10A). All food was provided to the subjects for the course of the study. The appearance of new symptoms following intervention was recorded and profiled microbial community diversity before and after intervention in duodenal aspirates and stool using 16S rRNA marker-based sequencing. In addition, changes in epithelial barrier function were measured by FITC dextran (4 kDa; measure of paracellular transport) flux across duodenal biopsies using an Ussing chamber.

The dietary intervention led to a decrease in fiber intake (25±1.8 g/day before; 9±0.18 g/day after; p<0.0001, paired t-test). All patients developed new symptoms with 80% developing GI symptoms during the dietary intervention and the symptoms resolved within a week of discontinuing the diet (Table 5). Three subjects with baseline SIBO tested negative after the intervention while five continued to have SIBO, and two subjects developed SIBO. SIBO resolution or new SIBO diagnosis following the intervention was not specifically associated with symptoms.

TABLE 5

| Symptom | Affected n (%) |
| --- | --- |
| Any | 15 (100) |
| Any GI | 12 (80) |
| Multiple (≥2) | 14 (93) |
| Stool change (freq/consist) | 11 (73) |
| Constipation (Rome III) | 6 (40) |
| Fatigue/↓Energy | 9 (60) |
| Only Fatigue/↓Energy | 3 (20) |

Figure 10C:
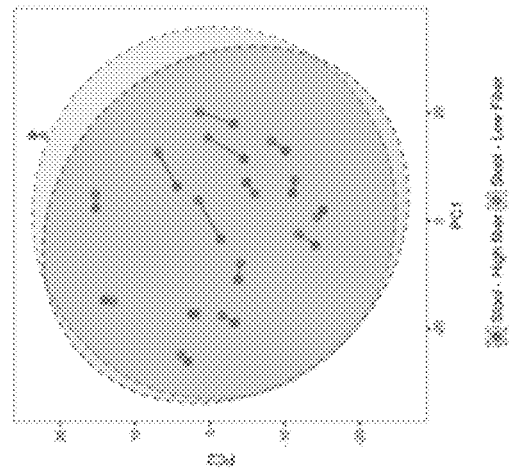
FIGS. 10A-10C contain data showing that dietary intervention impacts stool and small intestinal microbiota.
Figure 10B:
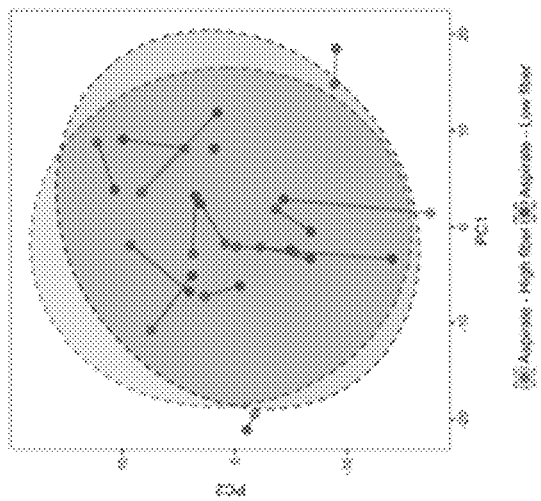
Figure 10A:
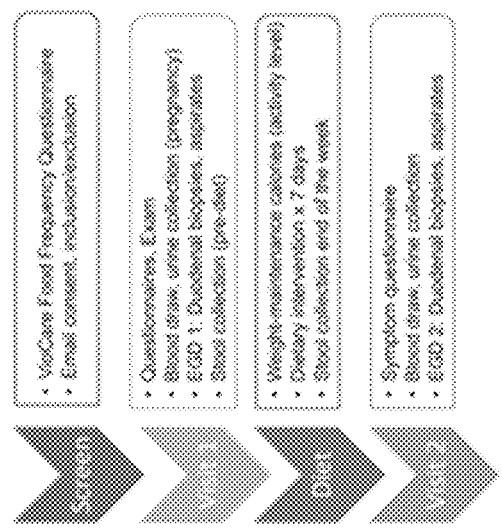

There was a significant correlation between the within-individual microbiome pre- and post-intervention both in duodenal aspirate and stool by Procrustes analysis (FIG. 10B, C). A significant inverse correlation was found between duodenal microbial phylogenetic diversity and duodenal permeability to 4 kDa FITC dextran (p=0.02, rho=−0.61, Spearman correlation; FIG. 11A), as well as decreased duodenal phylogenetic diversity in individuals who developed postprandial bloating (p=0.01, Mann Whitney U test; FIG. 11B), or abdominal discomfort that was relieved by a bowel movement (p=0.07, Mann Whitney U test; FIG. 11C).

Figure 13:
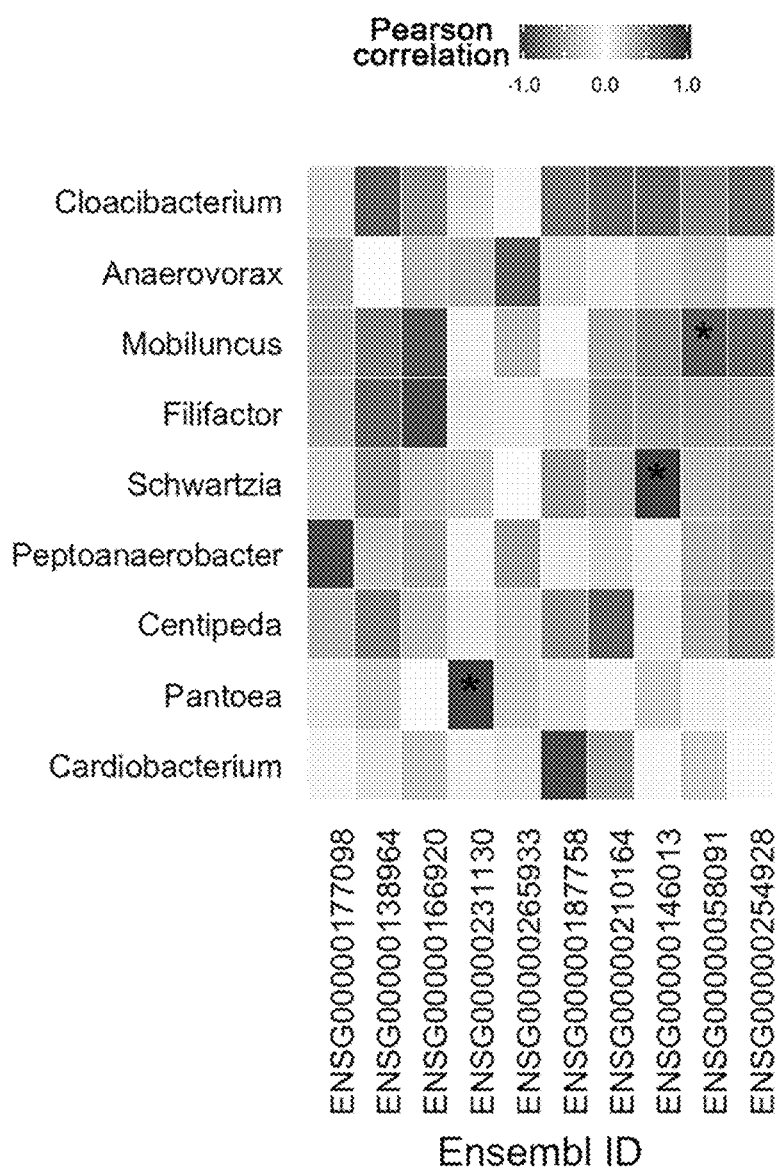
FIG. 13 contains data showing that changes in the duodenal aspirate microbiota correlate with mucosal gene expression. Correlation of the log fold change in duodenal gene expression following dietary intervention with the change in CLR abundance of genus-level taxa (shown are correlations with FDR-adjusted q-value <0.5; * indicates FDR-adjusted q<0.25).

To determine functional changes in the microbial communities following diet change, the metabolic content of duodenal aspirates and fecal samples collected before and after intervention was measured using $^1$H nuclear magnetic resonance (NMR) spectroscopy. Principal components analysis (PCA) was performed on these spectral profiles to identify biochemical variation associated with the intervention. Clustering was observed in the scores plot (FIG. 12A) from the PCA model comparing the pre- and post-intervention fecal profiles. This occurred along the first principal component (PC1) with the short chain fatty acids, acetate, propionate and butyrate, the amino acids, alanine and lysine, and succinate and glucose varying between the pre and post-intervention samples. The peak integrals for these metabolites were extracted from the NMR spectra (FIG. 12C) of fecal samples and acetate, butyrate and lysine were found to be significantly decreased in feces following the intervention (FDR q<0.05, Wilcoxon signed rank test, FIG. 11E). Although no intervention-related clustering was apparent in the PCA model constructed on the duodenal aspirate profiles (FIG. 12B), a decrease was observed in acetate in duodenal aspirates (FDR q=0.13, Wilcoxon signed rank test, FIG. 11D). These changes are consistent with alterations in microbial energy processing and a loss of fermentable fiber sources from the diet. Changes in duodenal mucosal gene expression are described in supplementary information (FIG. 13).

Figures 14A, 14B:
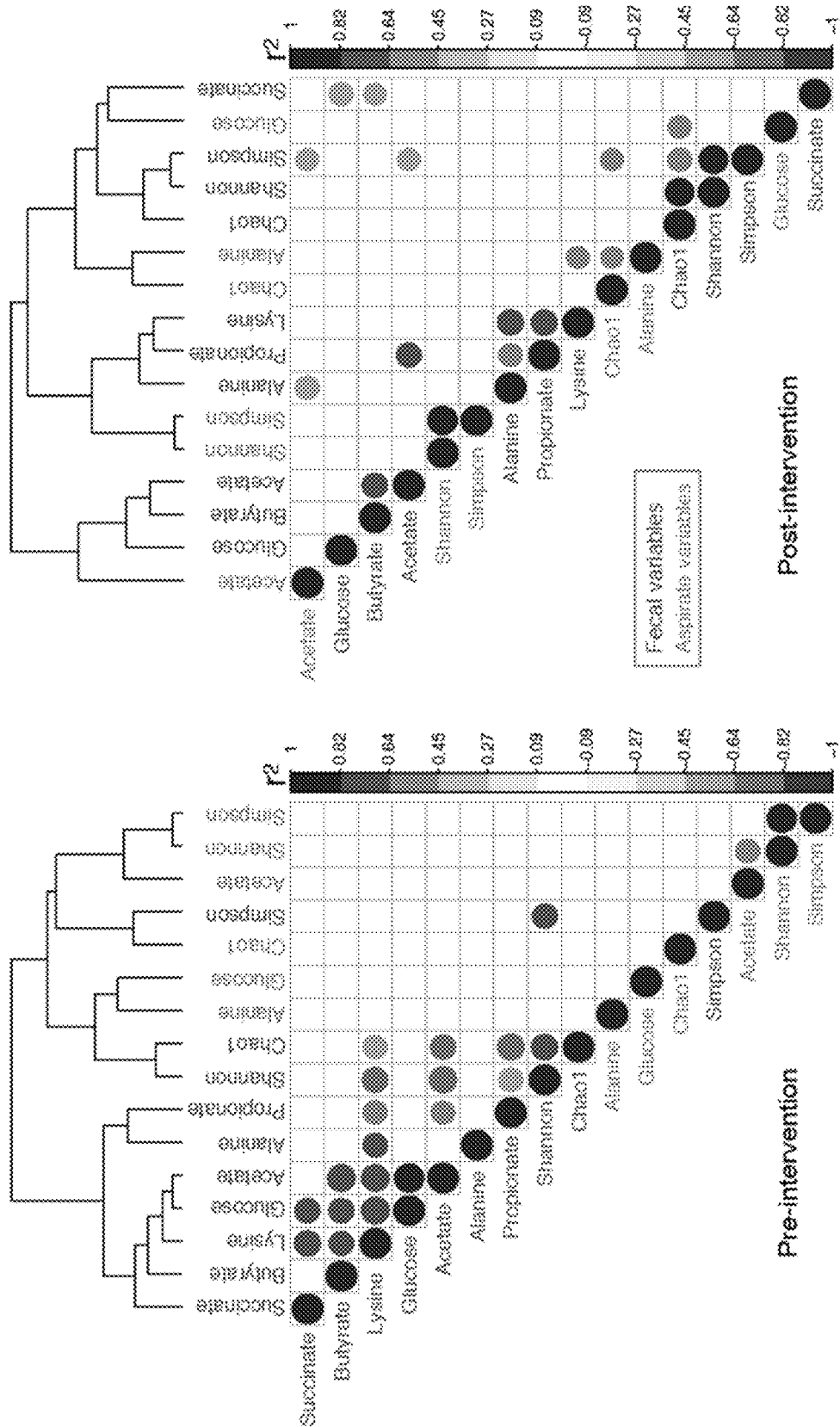
FIGS. 14A and 14B contain data showing that microbial diversity is associated with individual microbial metabolites. Individual correlodendograms showing statistical associations between fecal and duodenal metabolites and measures of alpha diversity in the duodenal and fecal microbiota pre-intervention (FIG. 14A) and post-intervention (FIG. 14B). Color intensity and size of the circle are proportional to the correlation coefficients (Spearman correlation). Significant correlations (p<0.05) are shown.

Separate correlation analyses were performed to identify statistical associations between the measured study variables before and after intervention. A number of significant associations were observed pre-intervention (p<0.05, Spearman correlation, FIG. 14A) including negative associations between fecal bacterial diversity (Chao1 and Shannon) and fecal acetate and propionate. In contrast, bacterial diversity in the duodenum (Shannon) was positively correlated with duodenal acetate pre-intervention. Post intervention (FIG. 14B), fecal bacterial diversity defined by the Simpson metric was negatively correlated with acetate in both the feces and aspirate samples while diversity measured by the Chao1 metric was positively correlated with duodenal glucose.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a mammal having a functional gastrointestinal disorder (FGID) using a targeted treatment approach, wherein said method comprises:
   (a) identifying said mammal as having a small intestinal microbiome (i) comprising two or more microbes selected from group A consisting of *Anaeroglobus* species, *Erwinia* species, *Escherichia* species, *Staphylococcus* species, *Scardovia* species, *Bifidobacterium* species, *Lactobacillus* species, *Olsenella* species, *Slackia* species, and *Shuttleworthia* species; and (ii) comprising reduced levels of two or more microbes selected from group B consisting of *Lachnoanaerobaculum* species, *Prevotella* species, *Leptotrichia* species, *Catonella* species, *Gemella* species, *Neisseria* species, *Haemophilus* species, and *Streptococcus* species; and
   (b) administering a probiotic to said mammal, wherein said probiotic comprises one or more of said microbes selected from said group B that were identified as having said reduced levels in said step (a).

2. The method of claim 1, wherein said mammal is a human.

3. The method of claim 1, wherein said FGID is irritable bowel syndrome (IBS).

4. The method of claim 1, wherein said identifying step comprises obtaining a sample from the small intestine of said mammal and determining the small intestinal microbiome within said sample.

5. The method of claim 4, wherein said sample is a fecal sample or a duodenal aspirate sample.

6. The method of claim 1, wherein said probiotic further comprises a microbe selected from group C consisting of *Megasphaera* species, *Peptostreptococcus* species, *Campylobacter* species, *Rothia* species, *Actinomyces* species, and *Granulicatella* species.

* * * * *

SEQUENCE LISTING

<160> NUMBER OF SEQ ID NOS: 2

<210> SEQ ID NO 1
<211> LENGTH: 52
<212> TYPE: DNA
<213> ORGANISM: Artificial Sequence
<220> FEATURE:
<223> OTHER INFORMATION: synthetic primer

<400> SEQUENCE: 1
tcgtcggcag cgtcagatgt gtataagaga caggtgccag cmgccgcggt aa        52

<210> SEQ ID NO 2
<211> LENGTH: 54
<212> TYPE: DNA
<213> ORGANISM: Artificial Sequence
<220> FEATURE:

```
<223> OTHER INFORMATION: synthetic primer

<400> SEQUENCE: 2
gtctcgtggg ctcggagatg tgtataagag acagggacta chvgggtwtc taat            54
```